(12) United States Patent
Davis et al.

(10) Patent No.: US 9,402,871 B2
(45) Date of Patent: Aug. 2, 2016

(54) LACTIC ACID BACTERIA AND THEIR USE IN SWINE DIRECT-FED MICROBIALS

(71) Applicant: DUPONT NUTRITION BIOSCIENCES APS, Copenhagen (DK)

(72) Inventors: Mari Ellen Davis, Waukesha, WI (US); Joshua M. Rehberger, Milwaukee, WI (US); Charles Maxwell, Springdale, AR (US); Thomas G. Rehberger, Wauwatosa, WI (US); Mike King, Oak Creek, WI (US)

(73) Assignees: DuPont Nutrition Biosciences APS, Copenhagen (DK); Board of Trustees of the University of Arkansas, Fayetteville, AR (US)

( * ) Notice: Subject to any disclaimer, the term of this patent is extended or adjusted under 35 U.S.C. 154(b) by 0 days.

(21) Appl. No.: 14/661,586

(22) Filed: Mar. 18, 2015

(65) Prior Publication Data
US 2015/0190436 A1   Jul. 9, 2015

Related U.S. Application Data

(62) Division of application No. 14/049,741, filed on Oct. 9, 2013, now Pat. No. 9,011,877, which is a division of application No. 12/685,979, filed on Jan. 12, 2010, now Pat. No. 8,563,295.

(60) Provisional application No. 61/143,990, filed on Jan. 12, 2009.

(51) Int. Cl.
| | | |
|---|---|---|
| *A61K 39/02* | (2006.01) |
| *A61K 35/744* | (2015.01) |
| *A23K 1/00* | (2006.01) |
| *A23K 1/18* | (2006.01) |
| *C07K 14/335* | (2006.01) |
| *C12Q 1/68* | (2006.01) |
| *C12R 1/01* | (2006.01) |
| *A61K 35/747* | (2015.01) |
| *A61K 35/12* | (2015.01) |

(52) U.S. Cl.
CPC ............... *A61K 35/744* (2013.01); *A23K 1/009* (2013.01); *A23K 1/184* (2013.01); *A23K 1/1893* (2013.01); *A61K 35/747* (2013.01); *C07K 14/335* (2013.01); *C12Q 1/689* (2013.01); *C12R 1/01* (2013.01); *A61K 35/12* (2013.01); *C12Q 2600/158* (2013.01)

(58) Field of Classification Search
None
See application file for complete search history.

(56) References Cited

U.S. PATENT DOCUMENTS

2004/0028665 A1*   2/2004   Garner .................... A23K 1/009
                                                    424/93.45

\* cited by examiner

*Primary Examiner* — Jennifer Graser
(74) *Attorney, Agent, or Firm* — Whyte Hirschboeck Dudek S.C.

(57) ABSTRACT

TRFs useful for identifying strains of interest are provided. A method of identifying one or more strain that can be used as a direct-fed microbial is also provided. One or more strain identified by the method is additionally provided. A method is also provided for administering to an animal an effective amount of the one or more strain. Additionally provided is an isolated strain chosen from at least one of *Lactobacillus acidophilus* strain P1B c6 (NRRL B-50103), *Lactobacillus salivarius* strain o246e 33w (NRRL B-50102), *Pediococcus acidilactici* strain o246e 42 (NRRL B-50171), and *Pediococcus acidilactici* strain P1J e3 (NRRL B-50101). An isolated strain having all of the identifying characteristics of one of the strains listed above is also provided. One or more strain can be administered as a direct-fed microbial to an animal. Methods of preparing a direct-fed microbial are also provided.

11 Claims, 3 Drawing Sheets

```
                        SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: 5' end of a portion of the 16S rRNA gene coding
      region of a lactic acid bacteria

<400> SEQUENCE: 1
agagtttgat ymtggctcag                                                  20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agagtttgat ymtggctcag                                                  20

<210> SEQ ID NO 3
<211> LENGTH: 15
<212> TYPE: DNA
<213> ORGANISM: Artificial Sequence
<220> FEATURE:
<223> OTHER INFORMATION: Primer

<400> SEQUENCE: 3
acgggcggtg tgtrc                                                       15
```

LACTIC ACID BACTERIA AND THEIR USE IN SWINE DIRECT-FED MICROBIALS

CROSS-REFERENCE TO RELATED APPLICATIONS

This application is a divisional patent application of U.S. patent application Ser. No. 14/049,741 filed Oct. 9, 2013, which is a divisional patent application of U.S. patent application Ser. No. 12/685,979 filed Jan. 12, 2010 and issued as U.S. Pat. No. 8,563,295 on Oct. 22, 2013, which claims priority under 35 U.S.C. §119(e) to U.S. Provisional Patent Application No. 61/143,990 filed Jan. 12, 2009; the entirety of each application referenced above is incorporated by reference herein.

BIBLIOGRAPHY

Complete bibliographic citations of the references referred to herein by the first author's last name and year of publication in parentheses can be found in the Bibliography section, immediately preceding the claims.

FIELD OF THE INVENTION

The invention relates to biological methods and products useful in agriculture. More particularly, though not exclusively, the present invention relates to lactic acid bacteria, methods of administering lactic acid bacteria to animals, such as pigs, and methods of making lactic acid bacteria.

DESCRIPTION OF THE RELATED ART

The swine industry has implemented the practice of early weaning for efficient and economical pig production (Wilson, 1995). The obvious consequence of weaning is the abrupt change in diet from sow's milk to solid feed and a change in the pigs' social environment (McCracken et al., 1995). There is reduced feed intake during the first week and associated adverse changes in the animal's gut anatomy and physiology such as villus atrophy, deeper crypts, and infiltration of the villus tip by immature enterocytes. Villus atrophy means that there is less absorptive area available for nutrient uptake and deeper crypts represent a large tissue turnover (Cera et al., 1988). Previous research has reported that villus height-to-crypt depth ratios are altered in response to different weaning environments and populations of resident gastrointestinal microflora populations (Tang et al., 1999). A disruption of the intestinal microflora often accompanies abrupt weaning, adversely impacting stability of the gastrointestinal tract, and this disruption may be the impetus for the alterations in feed intake and gut anatomy that lead to poor growth and compromised health during the post-weaning period (Dritz et al., 1996). Combined, these conditions have dramatic detrimental effects on piglet growth and health, negatively impacting the development of a mature digestive system and effective immune defense, with ramifications on the pig's growth performance through later production cycles.

Several approaches have evolved in modern swine production to address these issues while still capitalizing on the efficiency and economic benefits of early weaning, including management and diet changes. Early-weaning at an age of less than 21 days followed by removal of pigs to a second isolated site is commonly referred to as segregated early weaning (SEW). This approach reduces the incidence of a number of pathogens, thus reducing immunological stress, resulting in improved growth and higher efficiency of feed utilization (Fangman et al., 1997). This strategy has been successful in reducing the number of pathogens, but has not been successful in eliminating all pathogens. The premise is that pigs are removed from the sow while their immunity, as a consequence of maternal antibodies, is still high. This maternally derived passive immunity will prevent vertical transfer of indigenous pathogens. Whereas the gastrointestinal disruptions from abrupt weaning are not eliminated by SEW, the problems seem to be much less in prevalence and severity when pigs are weaned early and to an isolated facility off the farm site. This is likely a consequence of less pathogenic challenge to the pigs at weaning when their innate defenses are compromised.

Diet formulations utilizing good quality protein sources and additives to ease the weaning transition are an additional approach to protect piglet health. Two of the most prevalent options used are the inclusion of spray-dried plasma protein and in-feed antibiotics. The benefits of antibiotic supplementation to swine diets has been well documented, with the greatest improvements in responses occurring in response to antibiotic addition to weanling pigs compared to pigs in later growing stages (reviewed by Cromwell, 2001). The performance-enhancing benefits of spray-dried animal plasma (SDAP) are extensively documented as well within the scientific literature (reviewed by van Dijk et al., 2001a), and SDAP is particularly highly regarded as an ingredient in weanling pig starter diets. The addition of SDAP consistently results in improved body weight gain and feed intake, as well as reduction in post-weaning diarrhea, particularly during the one- to two-week time period following weaning (Coffey and Cromwell, 1995; van Dijk et al, 2001a; Wicker et al., 2004). Proposed mechanisms reported previously in the scientific literature include: improved diet palatability, improved digestibility of nutrients, the presence of beneficial growth factors, pathogen binding/blocking glycoproteins, neutralization of toxins; the presence of immunoglobulins, immunomodulation, improved intestinal morphology, and changes in gut microbial ecology (Bosi et al., 2001, 2004; Hammer et al., 2004; Mouricout et al., 1990; Nollet et al., 1999; Perez-Bosque et al., 2004; Roche et al., 2000; Torrallardona et al., 2003; van Dijk et al., 2001a; van Dijk et al., 2002b).

The effects of these and other dietary additives lend support to the concept that the effects of luminal nutrients and additives have less of a direct impact on the pig and instead act by mediating microbial shifts in response to exogenous nutrient availability (Gaskins, 2001). This has led to great interest in the use of direct-fed microbial (DFM) additives to aid the weaning transition by preventing the disruption of the gastrointestinal ecosystem that paves the way for pathogen invasion, thereby promoting growth and maintaining health in the young pig. Supplementation of *Bacillus* cultures has been reported to improve growth performance in weanling pigs (Yang et al., 2003; Kyriakis et al., 1999; Adami et al., 1997) by affording the pig protection against pathogenic challenges. Whereas most of the DFM additives commonly fed to swine are *Bacillus*-based, supplementation with lactobacilli also provide performance benefits to the young pig. *Salmonella*-challenged pigs supplemented with a five-strain combination of lactobacilli had improved weight gain, less severity of symptoms, and reduced fecal shedding of *Salmonella* compared to unsupplemented pigs that were challenged (Casey et al., 2007). Also, *Lactobacillus brevis* supplemented to the neonatal pig resulted in goblet cell maturation in the small intestine and dramatic improvements in body weight gain following weaning, that seem to be a consequence of control of inflammatory signals in the gut through toll-like receptor signaling (Davis et al., 2006, 2007). With the stigma of antibiotic resistance associated with growth promoting levels of antimicrobials fed to livestock and the use of animal byproducts like plasma protein with recent concerns regarding Transmissible Spongiform Encephalitis, supplementation of beneficial bacteria to provide some of the same benefits has gained popularity in the livestock industries.

Although there is a paucity of scientific support for their efficacy and limited understanding of their mode of action, supplementation with probiotic products has become increasingly popular in both human and agriculture sectors. Historically, probiotics originated from the concept that individuals that consumed large quantities of fermented dairy products, such as yogurt and cheese, were especially long-lived (Tannock, 2004). The majority of probiotic organisms are selected because they are easily propagated and readily available from food fermentation processes, with very little scientific support guiding their selection (Fuller, 1997). Therefore, bacteria used for DFM products for livestock species are not usually selected to provide bacterial organisms that would be ideally suited for the challenges present in livestock production systems.

What is needed are bacterial strains that are useful in pigs and other animals. Methods of making and using bacterial strains are also needed. In addition, DNA sequences for identifying these strains and methods of identifying strains with the DNA sequences are also needed.

SUMMARY OF THE INVENTION

The invention, which is defined by the claims set out at the end of this disclosure, is intended to solve at least some of the problems noted above.

A DNA sequence is provided. The DNA sequence includes a portion of the 16S rRNA gene coding region of a lactic acid bacteria, the 5' end of which includes the sequence of 5' AGAGTTTGATYMTGGCTCAG 3', the 3' end of which includes a restriction enzyme recognition site for one of Bfa I, Hae III, and Msp I. When the restriction enzyme recognition site is Bfa I, the DNA sequence has a length of about 99 base pairs to about 103 base pairs, about 268 base pairs to about 273 base pairs, about 260 base pairs to about 265 base pairs, about 279 base pairs to about 284 base pairs, about 278 base pairs to about 282 base pairs, or about 273 base pairs to about 277 base pairs. When the restriction enzyme recognition site is Hae III, the DNA sequence has a length of about 329 base pairs to about 334 base pairs, about 352 base pairs to about 357 base pairs, about 277 base pairs to about 282 base pairs, or about 335 base pairs to about 339 base pairs. When the restriction enzyme recognition site is Msp I, the DNA sequence having a length of about 188 base pairs to about 192 base pairs.

A method of identifying one or more strain that can be used as a direct-fed microbial is also provided. In the method, DNA is isolated from bacteria from the gastrointestinal tract of an animal. The DNA is amplified. The amplified DNA is analyzed with T-RFLP to generate TRF data. The TRF data is correlated to a characteristic of interest. Strains of interest are identified from the correlations. The presence of the TRF in the strain is confirmed.

One or more strain identified by the method is additionally provided. A method is also provided for administering to an animal an effective amount of the one or more strain.

In addition, an isolated *Pediococcus acidilactici* strain P1J e3 (NRRL B-50101) is provided, along with a combination including the isolated *Pediococcus acidilactici* strain P1J e3 (NRRL B-50101) and an isolated *Lactobacillus salivarius* strain o246e 33w (NRRL B-50102).

Additionally provided is an isolated strain chosen from at least one of *Lactobacillus acidophilus* strain P1B c6 (NRRL B-50103), *Lactobacillus salivarius* strain o246e 33w (NRRL B-50102), *Pediococcus acidilactici* strain o246e 42 (NRRL B-50171), and *Pediococcus acidilactici* strain P1J e3 (NRRL B-50101). An isolated strain having all of the identifying characteristics of one of the strains listed above is also provided.

Additional methods are provided. In one, an effective amount of at least one strain chosen from *Lactobacillus acidophilus* strain P1B c6 (NRRL B-50103), *Lactobacillus salivarius* strain o246e 33w (NRRL B-50102), *Pediococcus acidilactici* strain o246e 42 (NRRL B-50171), and *Pediococcus acidilactici* strain P1J e3 (NRRL B-50101) is administered to an animal.

Another method is a method of preparing a direct-fed microbial. In it, in a liquid nutrient broth, at least one strain chosen from *Lactobacillus acidophilus* strain P1B c6 (NRRL B-50103), *Lactobacillus salivarius* strain o246e 33w (NRRL B-50102), *Pediococcus acidilactici* strain o246e 42 (NRRL B-50171), and *Pediococcus acidilactici* strain P1J e3 (NRRL B-50101) is grown. The strain is separated from the liquid nutrient broth to form the direct-fed microbial.

BRIEF DESCRIPTION OF THE DRAWINGS

Exemplary embodiments of the invention are illustrated in the accompanying drawings.

Figure 1:
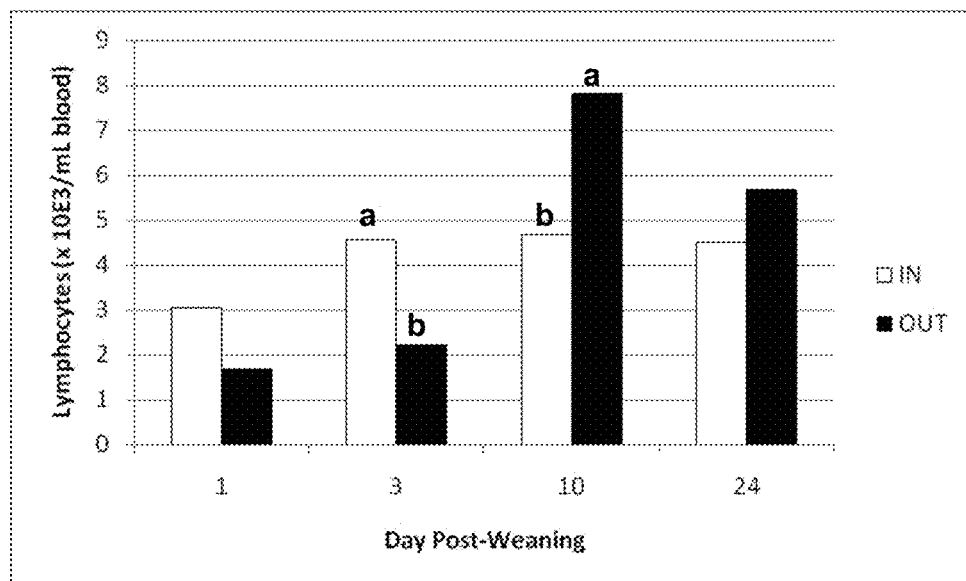
FIG. 1 is a graph displaying the concentration of lymphocytes on day 1, 3, 10, and 24 post-weaning (or 20, 22, 29 and 43 d of age) isolated from the peripheral blood of nursery pigs farrowed in conventional indoor facilities compared to those farrowed in outdoor facilities (Treatment×Day interaction, $P<0.01$; a,b, Means within each day with differing letters are different ($P<0.05$).

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

In accordance with the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Described herein are novel lactic acid bacteria strains and combinations thereof. The strains, alone or in combination, can be administered to animals, such as pigs. When fed to pigs, the strains provide many benefits. When the strains are fed to pregnant sows or gilts or to lactating sows, benefits are seen in their offspring. The strains also provide benefits when fed to pigs of other ages, such as nursery pigs and grow/finish pigs.

A method of identifying one or more strain that can be used as a direct-fed microbial (DFM) is also described herein. In the method, DNA is isolated from bacteria from gastrointestinal track of an animal. The DNA is amplified. The amplified DNA is analyzed with Terminal Restriction Fragment Length Polymorphism (T-RFLP) to generate terminal restriction fragment (TRF) data. The TRF data is correlated to a characteristic of interest. Strains of interest are identified from the correlations. The number of strains is reduced with RAPD PCR analysis of the strains or any other suitable method. The presence of the TRF in the strain is confirmed.

Terminal Restriction Fragments (TRFs):

Described herein are TRFs useful for identifying strains of interest. Those TRFs include, but are not limited to, a DNA sequence that includes a portion of the 16S rRNA gene coding region of a lactic acid bacterium. The 5' end of the DNA sequence includes the sequence of 5' AGAGTTTGATYMTGGCTCAG 3', and the 3' end includes a restriction enzyme recognition site for one of Bfa I, Hae III, and Msp I. When the restriction enzyme recognition site is Bfa I, the DNA sequence has a length of about 99 base pairs to about 103 base pairs, about 268 base pairs to about 273 base pairs, about 260 base pairs to about 265 base pairs, about 279 base pairs to about 284 base pairs, about 278 base pairs to about 282 base pairs, or about 273 base pairs to about 277 base pairs. When the restriction enzyme recognition site is Hae III, the DNA sequence has a length of about 329 base pairs to about 334 base pairs, about 352 base pairs to about 357 base pairs, about 277 base pairs to about 282 base pairs, or about 335 base pairs to about 339 base pairs. When the restriction enzyme recognition site is Msp I, the DNA sequence has a length of about 188 base pairs to about 192 base pairs.

Lactic Acid Bacteria:

Also described herein are strains of lactic acid bacteria that were identified using terminal restriction fragments (TRF): *Lactobacillus acidophilus* P1B c6, *L. salivarius* o246e 33w, *Pediococcus acidilactici* o246e 42, and *P. acidilactici* P1J e3. These strains were deposited at the Agricultural Research Service Culture Collection (NRRL), 1815 North University Street, Peoria, Ill., 61604 as follows. *Lactobacillus acidophilus* P1B c6 was deposited on Jan. 18, 2008 and received accession number NRRL B-50103, *L. salivarius* o246e 33w was deposited on Jan. 18, 2008 and received accession number NRRL B-50102, *Pediococcus acidilactici* o246e 42 was deposited on Aug. 29, 2008 and received accession number NRRL B-50171, and *P. acidilactici* P1J e3 was deposited on Jan. 18, 2008 and received accession number NRRL B-50101. Additional strains identified with the TRFs described herein are also within the scope of the invention.

A lactic acid bacteria strain, *Lactobacillus brevis* 1E1, can be used with one or more of the strains listed above. Strain 1E-1 (also written as strain 1E1) was isolated from the intestinal tract of a healthy, weaned pig. Strain 1E-1 is available from the microorganism collection of the American Type Culture Collection, 10801 University Blvd., Manassas, Va. 20110, under accession number PTA-6509, and was deposited on Jan. 12, 2005. All of the deposits were made under the provisions of the Budapest Treaty on the International Recognition of the Deposit of Microorganisms for the Purposes of Patent Procedure.

Strains having all the identifying characteristics (as provided below) of the strains listed above are also considered within the scope of the invention.

In brief, strains of lactic acid bacteria were identified using TRFs as follows with further details of this below in the Examples section. Pigs were separated into two groups with different conditions to produce differences in performance and immune measurements, e.g., specific immune subpopulations of immune cells. As used herein, "performance" refers to the growth of an animal measured by the following parameters: average daily weight gain, total weight gain, feed conversion, which includes both feed:gain and gain:feed, feed efficiency, mortality, and feed intake. "An improvement in performance" as used herein, means an improvement in at least one of the parameters listed above under the performance definition.

From the group of pigs having measurements for performance and immune characteristics, TRFs were identified from the lactic acid bacteria from their gastrointestinal tracks. These TRFs were present in the group of pigs having beneficial measurements and were absent in the group of pigs lacking beneficial measurements. The number of potentially useful strains was narrowed using RAPD PCR analysis. The existence of the TRFs in the narrowed group of strains was confirmed. Because those TRFs were found in the group of pigs having better measurements, the inventors believed that those strains should positively affect performance and/or immune modulation. When fed to animals, four strains of lactic acid bacteria were found to positively affect performance.

The strains can be fed alone or in combination. In one exemplary embodiment, strains *Lactobacillus acidophilus* P1B c6, *Lactobacillus salivarius* o246e 33w, and *Pediococcus acidilactici* P1J e3 are combined and administered to animals such as lactating sows and/or to piglets. In another exemplary embodiment, strains *Pediococcus acidilactici* P1J e3 and *Lactobacillus salivarius* o246e 33w are combined and administered. In another exemplary embodiment, *Pediococcus acidilactici* P1J e3 alone is administered to animals such as lactating sows and/or to piglets.

Direct-Fed Microbials:

A direct-fed microbial (DFM), which is used interchangeably throughout this disclosure with "probiotic," includes one or more strain of lactic acid bacteria listed above. One or more carrier or other ingredients can be added to the DFM. The DFM may be presented in various physical forms, for example, as a top dress, as a water soluble concentrate for use as a liquid drench or to be added to a milk replacer, gelatin capsule, or gels. In one embodiment of the top dress form, freeze-dried lactic acid bacteria fermentation product is added to a carrier, such as whey, maltodextrin, sucrose, dextrose, limestone (calcium carbonate), rice hulls, yeast culture, dried starch, and sodium silico aluminate. In one embodiment of the water soluble concentrate for a liquid drench or milk replacer supplement, freeze-dried lactic acid bacteria fermentation product is added to a water soluble carrier, such as whey, maltodextrin, sucrose, dextrose, dried starch, sodium silico aluminate, and a liquid is added to form the drench or the supplement is added to milk or a milk replacer. In one embodiment of the gelatin capsule form, freeze-dried lactic acid bacteria fermentation product is added to a carrier, such as whey, maltodextrin, sugar, limestone (calcium carbonate), rice hulls, yeast culture dried starch, and/or sodium silico aluminate. In one embodiment, the lactic acid bacteria and carrier are enclosed in a degradable gelatin capsule. In one embodiment of the gels form, freeze-dried lactic acid fermentation product is added to a carrier, such as vegetable oil, sucrose, silicon dioxide, polysorbate 80, propylene glycol, butylated hydroxyanisole, citric acid, ethoxyquin, and artificial coloring to form the gel.

To obtain the lactic acid bacteria and to form a DFM, the lactic acid bacteria can be fermented to an appropriate level. In a non-limiting example, that level is between about a $1\times10^9$ CFU/ml level to about a $1\times10^{10}$ CFU/ml level. These lactic acid bacteria can be grown in de Man, Rogosa and Sharpe (MRS) broth at 37° C. for 24 hours. The bacteria can be harvested by centrifugation, and the supernatant removed.

The pelleted lactic acid bacteria can then be fed as a DFM to an animal, such as a pig. In some embodiments, the DFM is fed to a sow, a gilt, a pre-weaned piglet, a post-weaned piglet, or a pig of any age. The lactic acid bacteria can be fed to a sow during the lactation period, although the lactic acid bacteria can be fed for different durations and at different times. When fed to a gilt or sow, the strains are transferred to piglets borne to the gilt or sow. It is believed that this is accomplished via the fecal-oral route and/or via other routes. In one embodiment, pelleted lactic acid bacteria are freeze-dried for direct feeding to the animal. In at least some embodiments, lactic acid bacteria are added to animal feed.

When fed to an animal, lactic acid bacteria become established in its gastrointestinal tract. About $1\times10^8$ CFU/animal/day to about $5\times10^{10}$ CFU/animal/day of lactic acid bacteria can be fed regardless of whether the total CFU is derived from one organism or a combination of organisms. In an exemplary embodiment, $1\times10^9$ total CFU/animal/day of lactic acid bacteria is fed regardless of whether the total CFU is derived from one organism or a combination of organisms. In one embodiment, equal amounts of each strain are used. In another embodiment, unequal amounts are used.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Conventional Versus Segregated Early Weaning Growth Performance Model

A model to provide separation in growth performance was established using pigs reared in off-site segregated early weaning management conditions compared to pigs reared conventionally on the same farm site in which birthing and rearing by the dam occurred. Eighty-eight crossbred barrows and gilts from 11 litters were weaned at 19 days of age. One group of 44 pigs were moved to the segregated nursery 12 km away from the sow herd, whereas the remaining pigs were moved to a nursery facility located at the pre-weaning location. Pigs were allotted into 16 pens at each facility and body weight and feed disappearance were measured on day 11, 18, and 25 after weaning to determine average daily gain (ADG), average daily feed intake (ADFI), and gain:feed. Four pigs from each facility were selected for sampling on day 1, 3, 11, and 25 after weaning, in which a blood sample was obtained via vena cava puncture for cell isolation and pigs were humanely euthanized to obtain gastrointestinal tract tissues for microbial analyses and immune cell isolation. Table 1 below illustrates the improved (P<0.10) average daily gain and average daily feed intake responses observed for pigs reared in a segregated early weaning management system compared to conventionally reared pigs, as well as the greater (P<0.01) pig body weight observed for segregated early weaned pigs at the end of the study (25 days after weaning).

TABLE 1

Growth performance responses of weanling pigs reared in an off-site segregated early weaning (SEW) management system compared to pigs reared conventionally on-site (CONV).

|  | CONV | SEW | SEM[1] | P= |
| --- | --- | --- | --- | --- |
| d 0 to 11 post-weaning |  |  |  |  |
| ADG, g | 217 | 388 | 12.37 | 0.001 |
| ADFI, g | 181 | 410 | 14.36 | 0.001 |
| Gain:feed | 1.47 | 0.94 | 0.21 | 0.088 |
| d 11 to 25 post-weaning |  |  |  |  |
| ADG, g | 466 | 470 | 21.30 | 0.904 |
| ADFI, g | 587 | 591 | 29.80 | 0.927 |
| Gain:feed | 0.83 | 0.86 | 0.06 | 0.737 |
| d 0 to 25 post-weaning |  |  |  |  |
| ADG, g | 383 | 442 | 23.66 | 0.081 |
| ADFI, g | 452 | 531 | 30.87 | 0.075 |
| Gain:feed | 0.85 | 0.83 | 0.09 | 0.585 |
| Pig weight, kg |  |  |  |  |
| Initial | 5.94 | 5.87 | 0.07 | 0.479 |
| d 11 | 8.10 | 9.51 | 0.27 | 0.001 |
| d 18 | 11.95 | 12.71 | 0.28 | 0.064 |
| d 25 | 15.85 | 17.38 | 0.35 | 0.003 |

[1]standard error of the mean (SEM)

Example 2

Outdoor vs Conventional Rearing Growth Performance Model

A second model was established to provide a more robust separation in growth performance between young pigs, in which pigs were either reared in conventional confinement farrowing facilities or farrowed in an outdoor management system. One hundred forty-four pigs were identified at each facility for the experiment. Conventionally reared pigs were located in Indiana, whereas the outdoor reared pigs were located in Colorado. Pigs at both facilities were of similar genetic background (PIC C-22×PIC 280). Six pigs from each facility, i.e., outdoor and indoor, were randomly selected to be sacrificed at each time interval of six and 14 days of age and 24 hrs prior to weaning (18 days of age) to measure gastrointestinal microbial populations and immune cell development during the pre-weaning period. One hundred and twenty-six pigs from each facility were weaned at 19 days of age and moved to an off-site nursery facility located in Arkansas. Upon arrival, pigs from each group were placed in separate rooms within the same facility to monitor growth performance during the post-weaning period while keeping the groups segregated to prevent exposure to the microflora between the two groups. Pig body weight and feed disappearance was determined at the end of each dietary phase, defined as Phase 1 (day 0 to 11 post-weaning), Phase 2 (day 11 to 25 post-weaning) and Phase 3 (day 25 to 39 post-weaning). Six pigs from each group were selected for sampling on day 1, 3, 7, 10, and 24 post-weaning, in which a blood sample was obtained via vena cava puncture for cell isolation and pigs were humanely euthanized to obtain gastrointestinal tract tissues for microbial analyses and immune cell isolation. Pigs farrowed in conventional sow facilities had numerically greater (5.18 vs. 5.74±0.28; $P=0.16$) initial body weight at weaning compared to pigs reared in outdoor facilities. However, pigs previously reared outdoors had greater ($P<0.01$) average daily gain, average daily feed intake, and body weight at the end of each phase than pigs farrowed in conventional confinement facilities (see Table 2 below).

TABLE 2

Average daily gain (ADG), average daily feed intake (ADFI), and gain:feed (G:F), of nursery pigs farrowed by sows housed in conventional, confinement facilities and sows housed in outdoor pasture facilities (with initial body weight of pigs used as a covariate in the analysis).

|  | Outdoor | Conventional | SEM[2] | P= |
|---|---|---|---|---|
| ADG, g | | | | |
| Phase 1 | 242 | 183 | 7 | <0.01 |
| Phase 2 | 515 | 411 | 14 | <0.01 |
| Phase 3 | 658 | 594 | 15 | <0.01 |
| Phase 1-3 | 486 | 408 | 10 | <0.01 |
| ADFI, g | | | | |
| Phase 1 | 338 | 246 | 10 | <0.01 |
| Phase 2 | 727 | 581 | 12 | <0.01 |
| Phase 3 | 1059 | 929 | 14 | <0.01 |
| Phase 1-3 | 720 | 596 | 10 | <0.01 |
| Gain:feed | | | | |
| Phase 1 | 0.724 | 0.751 | 0.022 | 0.40 |
| Phase 2 | 0.750 | 0.743 | 0.009 | 0.62 |
| Phase 3 | 0.661 | 0.672 | 0.006 | 0.17 |
| Phase 1-3 | 0.701 | 0.707 | 0.006 | 0.57 |
| Body weight, kg | | | | |
| Phase 1 | 8.14 | 7.47 | 0.08 | <0.01 |
| Phase 2 | 15.75 | 13.53 | 0.16 | <0.01 |
| Phase 3 | 25.58 | 22.27 | 0.26 | <0.01 |

[2]standard error of the mean (SEM)

Example 3

Immune Measurements and Flow Cytometric Analysis

Immune cells were isolated from blood and gastrointestinal samples and a battery of immune measurements were obtained from both of the growth performance models of Examples 1 and 2, including: differential white blood cell counts; peripheral blood mononuclear cell proliferation and cytokine proliferation; gastrointestinal morphology, goblet cell enumeration, and immunohistochemistry from jejunal tissue; and flow cytometric analysis on cells isolated from peripheral blood and jejunal tissue. Cell isolation methods and laboratory procedures have been previously published in the scientific literature (Davis et al., 2004; Brown et al., 2006a; Brown et al., 2006b). Antibody panels used to define immune cell subsets for immunohistochemistry and flow cytometric analyses are displayed in Table 3 below.

after weaning (management system x day interaction, $P<0.01$; FIG. 1). Furthermore, flow cytometric analysis of peripheral blood mononuclear cells revealed pigs reared in conventional confinement facilities during the lactation period had a greater proportion of leukocytes expressing the activation molecule, CD25, during the preweaning (40.90 vs. 26.95±4.99; $P<0.05$) and post-weaning (34.78 vs 19.26±4.55; $P<0.05$) periods. These data illustrate how the different rearing systems altered immune development both during the period when pigs within each system were separated (pre-weaning) and when the two groups were brought into a similar post-weaning management system. Differences were also evident in gastrointestinal development in which pigs reared in conventional confinement facilities had greater ($P<0.01$) villus height and lower ($P<0.05$) crypt depth within the duodenum before weaning compared to outdoor reared pigs, whereas duodenal villus height, crypt depth, and area were greater ($P<0.01$) in outdoor reared pigs compared to conventionally reared pigs after weaning (see Table 4 below).

TABLE 3

Monoclonal antibodies specific for swine leukocytes used to define cell surface molecule expression and differential populations of leukocytes derived from peripheral blood in immunohistochemistry and flow cytometric analyses.

| Monoclonal Antibodies[a] | Clone | Isotype | Specificy | Cell type(s) expressing molecule |
|---|---|---|---|---|
| CD2[1] | PG168A** | $IgG_3$ | CD2 | Virtually all thymocytes, T lymphocytes, and NK cells |
| CD3[2] | PPT3* | $IgG_1\kappa$ | $CD3_\epsilon$ | T lymphocytes |
| CD4[1,2] | 74-12-4* | $IgG_{2b}\kappa$ | CD4a | T helper lymphocytes |
| CD8[1,2] | 76-2-11* | $IgG_{2a}\kappa$ | CD8 α chain | Cytotoxic T lymphocytes |
| Monocyte/Granulocyte[1] | 74-22-15 | $IgG_{2b\kappa}$ | SWC3a | Granular leukocytes |
| CD25 (IL-2R)[1,2] | PGBL25A** | $IgG^1$ | CD25 (IL-2 R) | Interleukin-2 receptor; activated T and B lymphocytes |
| MHC-II[1,2] | MSA3** | $IgG_{2a}$ | MHC-II molecule | Monocytes/macrophages, B and T lymphocytes, etc. |
| CD21[2] | BB6-11C9.6* | $IgG_1\kappa$ | CD21 (complement receptor 2) | Mature circulating B lymphocytes |
| TCR1[2] | PGBL22A** | $IgG_1$ | Po-TCR1-N4 (γδ) | Antigen on T cells |

[a]Monoclonal antibodies are mouse anti-pig.
[1]Used for immunohistochemistry analysis.
[2]Used for flow cytometric analysis.
*Purchased from Southern Biotechnology Associates, Inc., Birmingham, AL.
**Purchased from Veterinary Medical Research and Development, Inc., Pullman, WA.

Differences in gastrointestinal development and health between conventionally and segregated early weaned pigs, as defined by intestinal morphology, goblet cell differentiation, and gastrointestinal immune cell populations have been reported previously in the literature (Brown et al., 2006a). Immune development was also altered by the two pre-weaning management systems utilized in the conventionally reared compared to the outdoor rearing growth model. Specifically, lymphocyte populations in the peripheral blood differed between the conventional and outdoor management systems during the post-weaning period, in which pigs reared previously outdoors had a lower ($P<0.05$) proportion of lymphocytes in the blood 3 days after weaning compared to conventionally reared pigs but a greater ($P<0.05$) proportion 10 days This is further evidenced by differences in immune cell development within the jejunum of the gastrointestinal tract. Examples of this include a greater (12.44 vs. 8.99±1.22; $P<0.05$) proportion of leukocytes expressing the CD25 activation molecule prior to weaning, a greater (25.08 vs. 16.49±3.49; $P<0.05$) proportion of lymphocytes expressing CD8 in pigs previously reared outdoors 24 days after weaning, and a greater proportion of leukocytes expressing the antigen presenting molecule, major histocompatability complex-II (MHC-II) as evidenced by immunohistochemistry analysis, during the pre-weaning (30.6 vs. 18.4±4.4) and post-weaning (26.0 vs. 35.1±3.7) periods when pigs were reared in outdoor systems compared to conventional confinement systems during the lactation period.

TABLE 4

Gastrointestinal morphology (crypt depth, villus height, and villus area) measurements from the duodenum, jejunum, and ileum of pigs farrowed in outdoor and indoor management systems

|  | Pre-Weaning | | | | Post-Weaning | | | |
| --- | --- | --- | --- | --- | --- | --- | --- | --- |
|  | Indoor | Outdoor | SEM[3] | P≤ | Indoor | Outdoor | SEM[4] | P≤ |
| Duodenum | | | | | | | | |
| Crypt depth, µm | 70.7 | 79.1 | 3.0 | 0.05 | 94.1 | 117.5 | 4.3 | 0.01 |
| Villus height, µm | 450.8 | 390.0 | 15.5 | 0.01 | 332.7 | 388.0 | 12.41 | 0.01 |
| Villus area, µm$^2$ | 48,267 | 42,100 | 2276 | 0.06 | 42,658 | 53,680 | 1968 | 0.01 |
| Jejunum | | | | | | | | |
| Crypt depth, µm | 75.3 | 71.8 | 3.66 | 0.50 | 98.8 | 107.2 | 4.1 | 0.16 |
| Villus height, µm | 398.5 | 376.1 | 16.6 | 0.35 | 330.7 | 352.7 | 13.6 | 0.26 |
| Villus area, µm$^2$ | 35,394 | 34,804 | 2153 | 0.85 | 37,917 | 43,980 | 2347 | 0.08 |
| Ileum | | | | | | | | |
| Crypt depth, µm | 68.0 | 73.1 | 3.0 | 0.23 | 103.5 | 114.9 | 4.9 | 0.11 |
| Villus height, µm | 288.4 | 422.2 | 106.1 | 0.38 | 508.0 | 308.8 | 118.4 | 0.24 |
| Villus area, µm$^2$ | 32,529 | 27,993 | 1704 | 0.07 | 30,364 | 35,448 | 1260 | 0.01 |

[3]standard error of the mean (SEM)
[4]standard error of the mean (SEM)

Example 4

Isolation and Identification of Gastrointestinal Bacteria

Tissue Processing. Gastrointestinal sections including the pars esophagus, duodenum, jejunum and ileum were collected for bacterial cell isolation Luminal material was removed from each gut section by washing twice with 25 mL of sterile washing buffer (0.3 mM $KH_2PO_4$, 1 mM $MgSO_4$, and 0.05% cysteine hydrochloride, pH 7.0). Tract sections were cut transversely with sterile forceps and any remaining luminal material was again removed with 25 mL sterile 0.1% Peptone dilution buffer. The gut section was placed in a sterile whirl-pak bag with 99 mL of sterile peptone dilution buffer and masticated in a stomacher for 30 seconds to release colonizing or mucus associated bacteria. The masticated solution was poured into a sterile 250 mL centrifuge tube withholding the gut section. Centrifugation at 13,170×g for 10 min. was performed on the bacterial cell-containing solution. Subsequently the supernatant was discarded and 10 mL of sterile MRS+10% glycerol broth was added to the pellet, resuspended and frozen at −20° C. until subsequent DNA isolation.

DNA Isolation.

Frozen post-weaning gastrointestinal section samples (N=128) were thawed on ice prior to DNA isolation. Solutions were vortexed for 30 seconds to yield a heterogeneous sample and to break up aggregated cells or cells that may have become associated with globule material during freezing. Two mL of mixed cells were then filtered through sterile 1M Whatman milk filter paper to remove globular material that interfered with the DNA isolation process. The DNA isolation process continued as follows: 0.5 mL of cells were added to a sterile 15 mL conical tube and washed with 15 mL of 50 mM Tris-HCl, 10 mM EDTA ($T_{50}E_{10}$) solution pH 7.5, followed by centrifugation at 2,485×g for 10 min. to remove PCR inhibiting substances. This washing and centrifugation step was repeated a second time. The pelleted cells were isolated following the directions of the Roche Genomic DNA Isolation Kit (Roche Diagnostics Corp., Indianapolis, Ind.), with slight modifications. All Phosphate Buffered Saline solutions were replaced with $T_{50}E_{10}$ and a 100 mg/mL lysozyme solution dissolved in $T_{50}E_{10}$ replaced the 5 mg/mL lysozyme solution recommended. After isolation, the DNA was quantified using a Picogreen dsDNA Quantitation kit (Molecular Probes, Eugene, Oreg.) and a TD-360 Mini-Fluorometer (Turner Biosystems, Sunnyvale, Calif.).

PCR Amplification and T-RFLP Analysis.

Amplification reactions using 50 ng of DNA from each gut section sample (with the exception of the pars esophagus) were performed in triplicate to provide adequate quantity of amplified product and to reduce PCR variation. The DNA from the pars esophagus section was often undetectable in this range, thus 2 µL from pars esophagus DNA isolation samples were added to the PCR reaction. A 5'-tetrachlorofluorescein labeled 8F domain primer (5' AGAGTTTGATYMTGGCTCAG 3') and a 1406R universal primer (5' ACGGGCGGTGTGTRC 3') were used to amplify a large portion of the 16S rRNA gene coding region (Baker, et al., 2003).

Reaction mixtures of 100 µL contained 1×PCR buffer, each deoxynucleoside triphosphate (dNTP) at a concentration of 280 µM, 1.5 mM $MgCl_2$, 12.5 pM of tetramethylammonium chloride (TMAC), 77 pM of each primer and 10 U of Platinum Taq (Invitrogen, Madison, Wis.). The high concentration of Taq was determined by our lab as a means to overcome the effect of minute amounts of PCR inhibitors. Positive and negative controls were included to monitor the effects of contaminating DNA found in commercial Taq enzymes. PCR conditions were 95° C. for 5 min, 30 cycles of denaturation at 94° C. for 30 s, annealing at 57.5° C. for 30 s, and extension at 72° C. for 120 s. The final cycle included a final extension at 72° C. for 7 min. Purity of PCR products was verified by running in a 1% agarose gel, staining with ethidium bromide and visualizing with a UV transilluminator. Fluorescently labeled PCR amplicons that were performed in triplicate from each sample were pooled and then purified from the primers and concentrated to 80 µL using a Qiagen PCR Clean Up Kit (Qiagen, Valencia, Calif.). Subsequently, the cleaned sample was split into four equal volumes. Three of the aliquots were then digested individually with 10 U of either Bfa I, Hae III, or Msp I individually at 37° C. for 4 hr., while the fourth aliquot was stored at −20° C. for a fourth restriction enzyme analysis if required. TRFs from digestions using Bfa I are denoted with the letter B, while the letter H is used to designate TRFs from Hae III and M for Msp I. All TRFs designations also include the size of the fragment, e.g., B100.79 is a 101 bpTRF generated with Bfa I. The use of three restriction enzymes improved the possibility of taxonomic identification of each TRF to the fewest number of bacterial species. Digested DNA was then cleaned with a Nucleotide Clean Up Kit (Qiagen) to improve resolution within the DNA sequencer. Two μL of the T-RFLP product was mixed with 3 μL of premix loading buffer that included 2 μL of BlueDextran/EDTA buffer (Applied Biosystems), 0.5 μL of GeneScan 500 TAMARA size standard (Applied Biosystems) and 0.5 μL of formamide. The T-RFs were analyzed by electrophoresis using a model ABI PRISM 377 Genetic Analyzer (Applied Biosystems) in Genescan mode (Laragen, Los Angeles, Calif.). GeneScan 3.1 software (Applied Biosystems) using the local Southern method was used to estimate fragment sizes. T-RFs with sizes outside of the ranges of 50-500 bp and T-RFs with peak heights below 50 relative fluorescence units were removed from the analysis.

Identification of Bacteria by T-RF Matching.

Sample T-RFLP data from each individual pig gut section from each sampling day was imported into the Bionumerics Gel Compar II package using the specialized T-RFLP extension (Applied Maths, Austin, Tex.). The Gel Compar II program was used to facilitate accurate band matching for all three restriction enzymes using a 0.5% position tolerance to define the bacterial species identified as operational taxonomic units (OTU) by T-RFs derived from the three restriction enzymes.

Example 5

Correlation of Gastrointestinal Bacteria to Growth Performance and Immune Characteristics Bacteria populations identified in both Examples 1 and 2 were separately correlated to growth performance factors and immune characteristic measurements from each trial. Methods for both analyses are described: OTUs were exported into Excel, converted to presence/absence as binary characters (0,1) or kept in quantitative form and $\log_{10}$ transformed to provide a normal distribution. Each data set was plotted and regressed against the performance data (ADG, ADFI, pig body weight, and feed efficiency) of each pig using pen as the experimental unit. The immune data results taken from each individual pig were $\log_{10}$ transformed and regressed against the T-RFLP data of each individual animal at each time point. These data were analyzed in two basic ways. First ordination methods with graphical plots were applied using Canoco Software Package (v 4.5—Biometris, Wageningen, Netherlands) to understand the relationship of community or population OTU as a whole to that of the studied parameters (gut section, performance, immune factors or management practice). Second, individual OTUs were regressed against each individual variable or parameter to determine direct univariate relationships. Constrained ordinal methods were applied allowing a determination of OTU population to variable relationships in the presence of dominating variables.

Scaling was focused on inter-species correlations and species scores were divided by the standard deviation. Sample and species data were centered but not standardized to avoid overweighting rare species. For immunological regressions, all immune factor data was $\log_{10}$ transformed prior to data analyses. Statistical significance of the species population (all species or OTUs) data in relationship to each environmental variable was determined by Monte Carlo Permutations using 499 unrestricted permutations. Statistical significance of each individual OTU relating to performance or immune results was also determined in univariate fashion performing General Linear Model (GLM)—Least Squares methodology with the SAS analysis package (SAS Institute, Cary, N.C.) and the Generalized Linear Model with Gaussian distribution was also applied using Canoco. The latter method is an extension of classical GLM methods. The OTUs with positive or negative performance relationships were then putatively identified by comparing against the results of all three restriction enzymes using both the Microbial Community Analysis (MiCA) at the University of Idaho and the T-RFLP Analysis Program (TAP; Marsh et al., 2000) from the Ribosomal Database Project. The use of three enzymes markedly reduced the number of potential bacterial species that might be indicative of the specific OTU set and helps to screen out the effect of potential pseudo-TRFs. Using both the population cluster regressions (RDA) and individual OTU regression (GLM) procedures, OTUs were analyzed, independent of variables such as treatment or day.

Example 6

Identification of Probiotic Bacteria Based on Correlations to Growth Performance Bacteria were selected as potential probiotics based upon significant correlations of TRFs to performance criteria, specifically average daily gain, pig body weight, and average daily feed intake. In the conventional vs. segregated early weaning management model described in Example 1, TRFs associated with *L. acidophilus* were most often positively correlated (P<0.05) to average daily gain during the early part of nursery (Phase 1), pig body weight during all three phases of the nursery period, and average daily feed intake during the early and late nursery period (see Table 5 below).

TABLE 5

Correlations associating TRFs identifying specific bacteria to growth performance measures during the post-weaning period of pigs reared in conventional on-site nursery facilities compared to pigs reared in a segregated early weaning system.[1]

|  | TRF | Average Daily Gain | | | Pig Body Weight | | | Average Daily Feed Intake | | |
| --- | --- | --- | --- | --- | --- | --- | --- | --- | --- | --- |
|  |  | Phase 1 | Phase 2a[2] | Phase 2b[3] | Phase 1 | Phase 2a[2] | Phase 2b[3] | Phase 1 | Phase 2a[2] | Phase 2b[3] |
| *L. acidophilus* | B100.79 | 0.008 |  |  | 0.0001 | 0.002 |  | 0.001 |  | 0.014 |
|  | H330.95 | 0.005 |  |  | 0.0001 | 0.002 | 0.0001 | 0.002 |  | 0.006 |
|  | M189.62 | 0.012 |  |  | 0.003 | 0.010 | 0.005 | 0.028 |  |  |
| *L. salivarius* | B262.58 |  |  | 0.018 |  |  |  |  | 0.010 |  |
|  | H280.34 |  | (0.008) |  | 0.014 | 0.024 | 0.013 | 0.035 |  | 0.038 |
|  | H279.80 |  |  |  |  |  |  |  |  |  |

TABLE 5-continued

Correlations associating TRFs identifying specific bacteria to growth performance measures during the post-weaning period of pigs reared in conventional on-site nursery facilities compared to pigs reared in a segregated early weaning system.[1]

|  |  | Average Daily Gain | | | Pig Body Weight | | | Average Daily Feed Intake | | |
|---|---|---|---|---|---|---|---|---|---|---|
|  | TRF | Phase 1 | Phase 2a[2] | Phase 2b[3] | Phase 1 | Phase 2a[2] | Phase 2b[3] | Phase 1 | Phase 2a[2] | Phase 2b[3] |
| P. acidilactici | B274.93 | | | | | | | | | |
|  | B281.86 | | | 0.083 | | | | | | 0.026 |
|  | H337.26 | | | | | | | | | 0.080 |
|  | M582 | | | | | | | | | |
| L. delbruedkii | B102.06 | | | | | | 0.091 | | | |
|  | H279.80 | | | | | | | | | |
|  | M179.95 | | | | 0.046 | 0.054 | 0.045 | | | |

[1]Values displayed represent P-values indicating significant (P < 0.10) positive (shown without parentheses) or negative (shown with parentheses) correlations of performance measures and specific TRFs during Phase 1 (d 0 to 10 post-weaning) and Phase 2 (d 10 to 24 post-weaning) of the nursery period.
[2]Phase2a = d 10 to 17 post-weaning.
[3]Phase2b = d 17 to 24 post-weaning.

Other TRFs associated with *L. salivarius*, *P. acidilactici*, and *L. delbruedkii* were also positively correlated (P<0.10) to improved gain, body weight and feed intake. In the model based on pigs reared in conventional confinement farrowing facilities compared to outdoor pasture farrowing facilities, several TRFs associated with *L. acidophilus* were again positively correlated (P<0.10) to average daily gain, pig body weight, and average daily feed intake (see Table 6 below).

TABLE 6

Correlations associating TRFs identifying specific bacteria to growth performance measures during the post-weaning period of pigs reared in conventional indoor farrowing facilities compared to pigs reared in an outdoor farrowing management system.[1]

|  |  | Day Post-Weaning | | | | | | | | | | | |
|---|---|---|---|---|---|---|---|---|---|---|---|---|---|
|  |  | Average Daily Gain | | | | Pig Body Weight | | | | Average Daily Feed Intake | | | |
|  | TRF | d 1 | d 3 | d 10 | d 24 | d 1 | d 3 | d 10 | d 24 | d 1 | d 3 | d 10 | d 24 |
| L. acidophilus | B100.66 | (0.068) | | | | 0.059 | 0.035 | (0.073) | 0.056 | | | | |
|  | H331.87 | (0.065) | | 0.079 | | | 0.071 | | | | | 0.079 | |
|  | M189.63 | | | | 0.087 | | | | | | | | (0.088) |
|  | B270.98 | (0.090) | 0.049 | | 0.089 | 0.059 | 0.018 | 0.063 | 0.027 | | | | |
|  | H336.55 | 0.059 | | 0.080 | | 0.064 | 0.085 | 0.029 | | 0.005 | 0.029 | 0.050 | |
|  | H354.76 | (0.063) | | | | 0.006 | 0.007 | 0.021 | 0.019 | 0.079 | 0.005 | | |
| L. salivarius | B261.76 | | 0.078 | | 0.062 | | (0.073) | | | 0.074 | | 0.082 | 0.041 |
|  | H278.38 | | | | | | | | | | | | |
|  | M568 | | | | | | | | | | | | |
| P. acidilactici | H336.55 | 0.059 | | 0.080 | | 0.064 | 0.085 | 0.029 | | 0.005 | 0.029 | 0.050 | |
|  | B280.97 | | | | | (0.017) | | 0.041 | | | | | |
|  | B274.94 | (0.078) | | | | | | | | | | | |
|  | M581 | | | | | | | | | | | | |
| L. delbruedkii | B102.55 | | 0.066 | | | | | | | | | | |
|  | H278.38 | | | | | | (0.073) | | | | | | |
|  | M179.75 | | | | | | | | | | | | |
| L. lactis | B261.76 | | 0.078 | | 0.062 | | | | | 0.074 | | 0.082 | 0.041 |
|  | H278.38 | | | | | | | | | | | | |
|  | M179.75 | | | | | | | | | | | | |
| L. crispatus | B265.00 | | | | | | | | | | | | |
|  | H245.90 | (0.063) | | | | | | | | | | 0.054 | (0.063) |
|  | M181.86 | | | | | | | 0.011 | | (0.096) | | (0.057) | 0.009 |

[1]Values displayed represent P-values indicating significant (P < 0.10) positive (shown without parentheses) or negative (shown in parentheses) correlations of performance measures and specific TRFs during Phase 1 (d 0 to 10 post-weaning) and Phase 2 (d 10 to 24 post-weaning) of the nursery period.

As in Example 1, other TRFs associated with *L. salivarius* and *P. acidilactici* were positively correlated (P<0.10) to growth performance. Also, a few TRFs associated with *L. delbruedkii*, *L. lactis*, and *L. crispatus* were positively correlated intermittently with growth performance factors in the indoor vs. outdoor model. Data associated with pre-weaning performance was not collected in the conventional vs segregated early weaning management model. TRFs associated with *L. acidophilus*, *P. acidilactici*, and *L. crispatus* were positively correlated (P<0.10) to piglet body weight during the pre-weaning period, specifically at 6, 13, and 18 days of age in the indoor vs. outdoor rearing model (see Table 7 below).

TABLE 7

Correlations associating TRFs identifying specific bacteria to pig body weight during the pre-weaning period of pigs reared in conventional indoor farrowing facilities compared to pigs reared in an outdoor farrowing management system.[1]

| | | Pig Body Weight Days of Age | | |
|---|---|---|---|---|
| | TRF | 6 | 13 | 18 |
| *L. acidophilus* | B100.66 | 0.023 | 0.049 | 0.024 |
| | H331.87 | 0.035 | 0.045 | 0.046 |
| | M189.63 | | | |
| | B270.98 | 0.011 | | 0.040 |
| | H336.55 | 0.094 | 0.042 | |
| | H354.76 | 0.001 | 0.006 | 0.006 |
| *P. acidilactici* | H336.55 | 0.094 | 0.042 | |
| | B280.97 | | | |
| | B274.94 | | | |
| | M581 | | | |
| *L. crispatus* | B265.00 | | | |
| | H245.90 | | 0.003 | |
| | M181.86 | | | |

[1]Values displayed represent P-values indicating significant (P < 0.10) positive (shown without parentheses) or negative (shown in parentheses) correlations of performance measures and specific TRFs during Phase 1 (d 0 to 10 post-weaning) and Phase 2 (d 10 to 24 post-weaning) of the nursery period.

Correlations to TRFs and day can be used to determine when the bacteria associated with specific TRFs should be present in the gastrointestinal tract of the pig, allowing the development of strategies to address timing of administration of a probiotic strain. In the conventional vs. segregated early weaning management model, TRFs associated with *L. acidophilus* were positively correlated (P<0.07) with presence just before weaning (18 days of age) and negatively correlated (P<0.05) with presence early in life (7 days of age) and after weaning (see Table 8 below).

TABLE 8

Correlations associating TRFs identifying specific bacteria to presence of the bacteria at specific of pigs reared in conventional on-site nursery facilities compared to pigs reared in a segregated early weaning (SEW) system.[1]

| | | Days of age | | | | | | | Management System | |
|---|---|---|---|---|---|---|---|---|---|---|
| | | 7 | 14 | 18 | 20 | 22 | 30 | 44 | Conventional | SEW |
| | TRF | | | | | | | (0.002) | (0.0001) | |
| *L. acidophilus* | B100.79 | | | 0.010 | (0.0001) | | | (0.058) | (0.039) | |
| | H330.95 | (0.0001) | | | (0.0001) | | | | (0.026) | |
| | M189.62 | (0.001) | | 0.005 | | | | | | |
| *L. salivarius* | B262.58 | | | 0.068 | (0.035) | | | (0.011) | (0.0001) | |
| | H280.34 | | | | | | | | | |
| | H279.80 | 0.087 | | (0.078) | (0.030) | | (0.002) | (0.002) | (0.0001) | (0.0001) |
| *P. acidilactici* | B274.93 | | | | | | | | | |
| | B281.86 | | | | | | | | | |
| | H337.26 | | | 0.001 | (0.016) | (0.056) | 0.0001 | | | |
| | M582 | | | | | | | | | |
| *L. delbruedkii* | B102.06 | | | | | | | | | |
| | H279.80 | 0.087 | | (0.078) | (0.030) | | (0.002) | (0.002) | (0.0001) | (0.0001) |
| | M179.95 | | 0.017 | | (0.007) | | | (0.0001) | (0.001) | (0.039) |

[1]Values displayed represent P-values indicating significant (P < 0.10) positive (shown without parentheses) or negative (shown in parentheses) correlations of age of pig and presence of specific TRFs.

In contrast, TRFs associated with *L. delbruedkii* were positively correlated (P<0.10) with presence early in life (7 and 14 days of age), but negatively correlated (P<0.10) with presence 18 days of age and later. Some TRFs associated with *L. salivarius* and *P. acidilactici* were positively and negatively correlated (P<0.10) to presence on various days during the pre- and post-weaning periods. In the indoor vs. outdoor rearing model, TRFs associated with *L. acidophilus* displayed clear negative correlations with presence before weaning and during the early weaning transition (20 days of age) and positive correlations with presence after 22 days of age (see Table 9 below). Although not as clearly separated between pre- and post-weaning periods, generally TRFs associated with *L. salivarius, L. delbruedkii, L. lactis,* and *L. crispatus* were positively correlated (P<0.05) with presence at 22 days of age and after, whereas *P. acidilactici* was positively correlated (P<0.05) with presence pre-weaning and at the weaning transition.

TABLE 9

Correlations associating TRFs identifying specific bacteria to the presence of the bacteria at specific ages and management systems of pigs reared in conventional indoor farrowing facilities compared to pigs reared in an outdoor farrowing management system.[1]

| | | Days of age | | | | | | | Management System | |
|---|---|---|---|---|---|---|---|---|---|---|
| | TRF | d 6 | 13 | 18 | 20 | 22 | 29 | 43 | Outdoor | Indoor |
| *L. acidophilus* | B100.66 | (0.023) | (0.027) | (0.037) | (0.013) | 0.002 | 0.0001 | 0.017 | | |
| | H331.87 | | | (0.041) | (0.018) | 0.045 | 0.006 | | (0.087) | 0.087 |
| | M189.63 | | | (0.083) | (0.030) | 0.007 | 0.049 | | | |
| | B270.98 | | | (0.094) | (0.090) | 0.008 | 0.066 | | | |
| | H336.55 | (0.057) | 0.016 | | 0.044 | 0.020 | | | | |
| | H354.76 | | | (0.068) | (0.064) | 0.001 | 0.058 | | | |
| *L. salivarius* | B261.76 | | | | | 0.024 | | | 0.047 | (0.047) |
| | H278.38 | | | | | (0.078) | 0.022 | | | |
| | M568 | | | | | | | | | |
| *P. acidilactici* | H336.55 | (0.057) | 0.016 | | 0.044 | 0.020 | | | | |
| | B280.97 | | | | 0.0001 | | | | | |
| | B274.94 | (0.053) | | (0.078) | | | | | | |
| | M581 | | | | | | | | | |
| *L. delbruedkii* | B102.55 | (0.001) | (0.003) | | | 0.027 | 0.0001 | 0.037 | | |
| | H278.38 | | | | | (0.078) | 0.022 | | | |
| | M179.75 | | | | | | | | | |
| *L. lactis* | B261.76 | | | | | 0.02 | | | 0.047 | (0.047) |
| | H278.38 | | | | | | | | | |
| | M179.75 | | | | | | | | | |
| *L. crispatus* | B265.00 | | | | | 0.058 | 0.001 | | (0.015) | 0.015 |
| | H245.90 | | | | | | | | (0.004) | 0.004 |
| | M181.86 | | | | (0.060) | | | | | |

[1]Values displayed represent P-values indicating significant (P < 0.10) positive (shown without parentheses) or negative (shown in parentheses) correlations of age of pig and presence of specific TRFs.

Example 7

Identification of Probiotic Bacteria Based on Correlations to Immune Characteristics Correlations can be made associating specific TRFs with immune populations within the systemic circulation (peripheral blood) and the gastrointestinal tract of pigs, allowing the prediction of how administration of the probiotic bacteria impact immune characteristics of these tissues in the young pig. Immune populations positively and negatively associated with specific TRFs from both growth models are listed in Table 10 and Table 11 below. Generally, TRFs associated with potential probiotic bacteria correlated positively ($P \leq 0.05$) to activated, memory, and gamma-delta T cell subsets in peripheral blood and the gastrointestinal tract.

TABLE 10

Correlations associating TRFs identifying specific bacteria to immune cell populations in the peripheral blood and gastrointestinal tract (GIT) of pigs reared in conventional on-site nursery facilities and pigs reared in a segregated early weaning (SEW) system.[1]

| Bacterial Species | TRF | Positively Correlated | Negatively Correlated |
|---|---|---|---|
| *L. acidophilus* | B100.79 | 1) Blood-Cytotoxic T cells ($CD8^+CD4^+$; $CD2^+CD8^+CD4^-$; $CD25^+CD8^+CD4^-$)<br>2) Blood-Activated memory subset ($CD25^+CD8^+CD4^+$)<br>3) Blood-Gamma-delta T cells ($TCR1^+CD8^-CD4^-$)<br>4) GIT-Memory T cell subset ($CD8^+CD4^+$) | 1) Blood-T helper cells ($CD3^+CD4^+$)<br>2) GIT-Activated lymphocytes ($CD25^+CD8^-CD4^-$) |
| | H330.95 | 1) Blood-Gamma-delta T cells ($CD8^-CD4^-TCR1^+$)<br>2) Blood-Memory T cell subset ($CD4^+CD8^+TCR1^-$) | 1) Blood-Activated lymphocytes ($CD25^+CD8^-CD4^-$)<br>2) Blood-Cytotoxic T cells ($CD2^+CD8^+CD4^-$) |
| | M189.62 | 1) Blood-Memory T cell subset ($CD2^+CD8^+CD4^+$)<br>2) GIT-Activated memory T cell subset ($CD25^+CD8^+CD4^+$)<br>3) GIT-Gamma-delta T cells ($CD4^+CD8^+TCR1^+$; $TCR1^+CD8^-CD4^-$) | 1) Blood-T lymphocytes ($CD3^+CD4^-$)<br>2) Blood-Gamma-delta T cells ($TCR1^+CD8^+CD4^-$)<br>3) Blood-Activated lymphocytes ($CD25^+CD8^-CD4^-$)<br>4) GIT-Cytotoxic T cells ($CD8^+CD4^-$)<br>5) GIT-Gamma-delta T cells ($TCR1^+CD8^+CD4^+$) |
| *L. salivarius* | B262.58 | 1) Blood-Activated lymphocytes ($CD25^+CD8^-CD4^-$)<br>2) GIT-Activated T helper cells ($CD4^+CD25^+CD8^-$) | 1) Blood-Leukocytes with antigen-presenting capacity (MHCIr)<br>2) Blood-T lymphocytes ($CD3^+CD4^+$; $CD2^+CD4^-CD8^-$)<br>3) GIT-T helper cells ($CD2^+CD4^+CD8^-$) |
| | H279.80 | 1) Blood-Gamma-delta T cells ($TCR^+$; $CD4^+TCR1^+CD8^-$)<br>2) GIT-Gamma-delta T cell memory subset ($TCR1^+CD8^+CD4^+$) | 1) Blood-Leukocytes with antigen-presenting capacity ($MHCII^+$)<br>2) Blood-Activated lymphocytes ($CD25^+$)<br>3) Blood-T helper cells ($CD3^+CD4^+$)<br>4) GIT-T lymphocytes ($CD2^+CD8^-CD4^-$)<br>5) GIT-Activated lymphocytes ($CD25^+CD8^-CD4^-$)<br>6) GIT-Memory T cell subset ($CD8^+CD4^+CD25^-$) |
| *P. acidilactici* | B274.93 | 1) Blood-Gamma-delta T cells ($CD4^+TCR1^+CD8^-$)<br>2) GIT-Cytotoxic T cells ($CD8^+CD4^-$)<br>3) GIT-Activated lymphocytes ($CD25^+CD8^-CD4^-$)<br>4) GIT-Gamma-delta T cells ($TCR1^+CD8^-CD4^-$) | 1) Blood-T lymphocytes ($CD3^+CD4^-$; $CD2^+CD4^-CD8^-$)<br>2) Blood-T helper cells ($CD4^+$)<br>3) Blood-Gamma-delta T cells ($TCR1^+$)<br>4) Blood-Activated lymphocytes ($CD25^+CD4^-CD8^-$)<br>5) GIT-T lymphocytes ($CD2^+CD4^-CD8^-$)<br>6) GIT-Memory T cell subset ($CD4^+CD8^+CD2^+$) |
| | H337.26 | 1) Blood-Cytotoxic T cells ($CD2^+CD8^+CD4^-$) | 1) Blood-Gamma-delta T cells ($CD8^+TCR1^+CD4^-$; $TCR1^+CD8^+CD4^-$)<br>2) Blood-T helper cells ($CD3^+CD4^+$; $CD4^+CD2^+CD8^-$) |

[1] Immune cell populations listed are positively or negatively correlated to the specified TRF at a significance level of $P \leq 0.05$.

TABLE 11

Correlations associating TRFs identifying specific bacteria to immune cell populations in the peripheral blood and gastrointestinal tract (GIT) of pigs reared in conventional confinement farrowing facilities and pigs farrowed in an outdoor pasture management system.[1]

| Bacterial Species | TRF | | Positively Correlated | | Negatively Correlated |
|---|---|---|---|---|---|
| *L. acidophilus* | B100.66 | 1) | Blood-Activated lymphocytes (CD25$^+$CD8$^-$CD4$^-$; CD25$^+$CD8$^+$CD4$^-$; CD25$^+$CD8$^+$CD4$^+$; CD4$^+$CD8$^+$CD25$^+$; MHCII$^+$CD3$^+$) | | |
| | | 2) | Blood-Gamma-Delta T cells (CD4$^+$CD8$^+$TCR1$^+$) | | |
| | | 3) | Blood-Memory T cell subset (CD8$^+$CD4$^+$) | | |
| | | 4) | Blood-B cells (CD21$^+$CD25$^-$;CD21$^+$CD25$^+$) | | |
| | | 5) | GIT-Activated lymphocytes (CD25$^+$CD8$^+$CD4$^+$;CD4$^+$CD8$^+$CD25$^+$;CD8$^+$CD25$^+$CD4$^-$;CD25$^+$CD8$^+$CD4$^+$; CD4$^+$CD25$^+$CD8) | | |
| | | 6) | GIT-Gamma-delta T cells (TCR1$^+$CD8$^+$CD4$^+$; CD4$^+$CD8$^+$TCR1$^+$; CD8$^+$TCR1$^+$CD4$^-$; CD8$^+$TCR1$^+$CD4$^-$; TCR1$^+$CD8$^-$CD4$^-$) | | |
| | | 7) | GIT-Memory T cell subsets (CD4$^+$CD8$^+$TCR1$^-$; CD4$^+$CD8$^+$) | | |
| | H331.87 | 1) | Blood T cells (CD3$^+$MHCII$^-$) | 1) | GIT-B cells (CD21$^+$CD25$^+$) |
| | | 2) | Blood-Activated lymphocytes (CD21$^+$CD25$^+$; CD25$^+$CD21$^-$; CD25$^+$CD8$^+$CD4$^+$; CD25$^+$CD8$^+$CD4$^-$; CD25$^+$CD8$^-$CD4$^+$) | | |
| | | 3) | GIT-Activated T lymphocytes (CD25$^+$CD21$^-$; CD4$^+$CD25$^+$CD8$^-$; CD25$^+$CD4$^+$CD8) | | |
| | | 4) | GIT-Memory T cells (CD4$^+$CD8$^+$CD25$^-$; CD8$^+$CD4$^+$ | | |
| | | 5) | GIT-Gamma-delta T cells (CD4$^+$TCR1$^+$CD8$^-$; TCR1$^+$CD4$^+$CD8) | | |
| | M189.63 | 1) | Blood-T cells (MHCII$^+$CD3$^+$) | 1) | GIT-B cells (CD21$^+$CD25$^-$) |
| | | 2) | Blood-Activated lymphocytes (CD21$^+$CD25$^+$;CD25$^+$CD21$^-$) | 2) | GIT-Gamma-delta T cells (TCR1$^+$CD8$^+$CD4$^-$; CD4$^+$CD8$^+$TCR1$^+$) |
| | | 3) | GIT-T helper cells (CD4$^+$) | | |
| | | 4) | GIT-Activated T cells (CD25$^+$CD21$^-$; CD4$^+$CD25$^+$CD8$^-$; CD25$^+$CD8$^-$CD4$^-$; CD25$^+$CD4$^+$CD8) | | |
| | | 5) | GIT-Gamma-delta T cells (CD8$^+$TCR1$^+$CD4$^-$; TCR1$^+$CD4$^+$CD8$^-$ | | |
| | B270.98 | 1) | Blood-T cells (CD3$^+$; MHCII$^+$CD3$^+$; CD3$^+$MHCII$^-$; CD3$^+$CD8$^-$) | 1) | Blood-Activated lymphocytes (CD25$^+$CD4$^-$CD8$^-$) |
| | | 2) | Blood-T helper cells (CD4$^+$CD8$^-$) | | |
| | | 3) | Blood-Activated lymphocytes (CD21$^+$CD25$^+$; CD25$^+$CD21$^-$) | | |
| | | 4) | GIT-T cells (CD3$^+$) | | |
| | | 5) | GIT-T helper cells (CD4$^+$) | | |
| | | 6) | GIT-Activated lymphocytes (CD25$^+$CD8$^-$CD4$^-$; CD25$^+$CD21$^-$;CD25$^+$CD4$^+$CD8$^-$) | | |
| | | 7) | GIT-Gamma-delta T cells (TCR1$^+$CD4$^-$CD8$^-$; | | |
| | H336.55 | 1) | Blood-B and T lymphocytes (CD3$^+$; CD3$^+$MHCII$^+$; CD21$^+$CD25$^-$) | | |
| | | 2) | Blood-Activated lymphocytes (CD25$^+$; CD25$^+$CD8$^+$CD4$^+$;CD25$^+$CD21$^+$; CD25$^+$CD21$^-$; CD8$^+$CD25$^+$CD4$^-$; CD25$^+$CD4$^-$CD8$-$; CD25$^+$CD8$^+$CD4$^-$) | | |
| | | 3) | Blood-Gamma-delta T cells (TCR1$^+$CD8$^+$CD4$^-$; TCR1$^+$CD4$^-$CD8$^-$) | | |
| | | 4) | GIT-Activated lymphocytes (CD25$^+$CD21$^-$; CD25$^+$CD4$^-$CD8$^-$) | | |
| | | 5) | GIT-Gamma-delta T cells (TCR1$^+$CD4$^+$CD8$^-$; | | |
| | H354.76 | 1) | Blood-T cells (CD3$^+$MHCII$^-$; CD3$^+$CD8$^-$) | 1) | Blood-Memory T cell subset (CD4$^+$CD8$^+$) |
| | | 2) | Blood-Activated lymphocytes (CD21$^+$CD25$^+$; CD25$^+$CD21$^-$; CD3$^+$MHCII$^+$) | | |
| | | 3) | GIT-T lymphocytes (CD3$^+$) | | |
| | | 4) | GIT-T helper cells (CD4$^+$) | | |
| | | 5) | GIT-Activated T cells (CD25$^+$CD4$^+$CD8$^+$) | | |
| | | 6) | GIT-Memory T cell subset (CD4$^+$CD8$^+$TCR1$^-$) | | |
| *L. salivarius* | B261.76 | 1) | Blood-T cells (MHCII$^+$CD3$^+$) | 1) | Blood-Leukocytes with antigen-presenting capacity (MHCII$^+$) |
| | | 2) | GIT-T helper cells (CD4$^+$CD8$^-$) | | |
| | H278.38 | 1) | Blood-B cells (CD21$^+$CD25$^-$) | 1) | Blood-Gamma-delta T cells (TCR1$^+$CD4$^+$CD8$^-$) |
| | | 2) | Blood-Gamma-delta T cells (TCR1$^+$CD8$^-$CD4$^-$; CD8$^+$TCR1$^+$CD4$^-$) | | |
| | | 3) | Blood-Activated lymphocytes (CD25$^+$CD8$^-$CD4$^-$) | | |
| | | 4) | GIT-Gamma-delta T cells (TCR1$^+$CD4$^+$CD8$^-$; TCR1$^+$CD8$^+$CD4$^+$) | | |
| *P. acidilactici* | H336.55 | | See *L. acidophilus* | | |
| | B280.97 | 1) | GIT-B cells (CD21$^+$CD25$^-$) | 1) | Blood-Leukocytes with antigen-presenting capacity (MHCII$^+$) |
| | | 2) | GIT-Activated T cells (CD25$^+$CD8$^+$CD4$^-$) | 2) | GIT-Activated T cells (CD25$^+$CD4$^+$CD8$^-$; |
| | | 3) | GIT-Gamma-delta T cells (TCR1$^+$CD8$^+$CD4$^-$) | | |

TABLE 11-continued

Correlations associating TRFs identifying specific bacteria to immune
cell populations in the peripheral blood and gastrointestinal tract (GIT) of pigs reared in conventional
confinement farrowing facilities and pigs farrowed in an outdoor pasture management system.[1]

| Bacterial Species | TRF | Positively Correlated | Negatively Correlated |
|---|---|---|---|
|  | B274.94 | 1) Blood-T cells ($CD3^+MHCII^-$; $CD8^+CD3^+$; $CD4^+CD8^-$; $CD3^+CD8^-$) | $CD4^+CD25^+Cd8^-$) |
|  |  | 2) Blood-B cells ($CD21^+CD25^+$; $CD21^+$) |  |
|  |  | 3) Blood-Gamma-delta T cells ($TCR1^+CD4^+CD8^-$; |  |
|  |  | 4) Blood-Memory T cell subsets ($CD8^+CD4^+$; $CD25^+CD8^+CD4^+$) |  |
|  |  | 5) GIT-Memory T cell subsets ($CD8^+CD4^+$; $CD4^+CD8^+TCR1^-$; $CD4^+CD8^+CD25^-$; |  |
|  |  | 6) GIT-Activated lymphocytes ($CD25^+CD8^-CD4^-$; $CD4^+CD8^+CD25^+$; $CD25^+CD4^+CD8^-$; $CD25^+CD4^+CD8^-$; $CD25^+CD21^-$) |  |
|  |  | 7) GIT-Gamma-delta T cells ($CD8^+TCR1^+CD4^-$; $CD4^+CD8^+CD25^+$; $CD4^+CD25^+CD8^-$; $TCR1^+CD4^-CD8^-$) |  |

[1] Immune cell populations listed are positively or negatively correlated to the specified TRF at a significance level of $P \leq 0.05$.

Example 8

Strain Identification of Probiotic Bacteria Through RAPD PCR Analysis

Intestinal samples that had yielded high peak heights for the TRFs of interest were selectively plated for lactic acid producing bacteria. Colonies were picked into broth and grown for 24 hours at which point DNA was isolated from the cell culture. Similarity of the isolates was evaluated by comparing RAPD PCR fingerprints of a 5'-tetrachlorofluorescein labeled 8F domain primer (5' AGAGTTTGATYMTGGCT-CAG 3') and a 1406R universal primer (5' ACGGGCGGT-GTGTRC 3'). TRFLP using Bfa I, Hae III, and Msp I was also performed on the isolates to ensure that they possessed the TRFs of interest. The TRFs of interest were all of the TRFs in Tables 5, 6, 7, and 8 that were associated with increased performance. The sizes of the TRFs in Tables 5 and 6 from the On-Site/Off-Site trial and the Indoor/Outdoor trial are slightly different due to position tolerance and optimization settings used in the Bionumerics software but were considered to be the same during the strain selection process. Table 12 shows the TRFs of interest with the TRF length and the TRF length plus and minus 2 basepairs to account for the slight differences noted above. The inventors believe that there is about 90% sequence identity when comparing a TRF sequence from one lactic acid bacteria strain compared to a TRF sequence from another lactic acid bacteria strain if the strains have the same TRF.

Figure 2A:
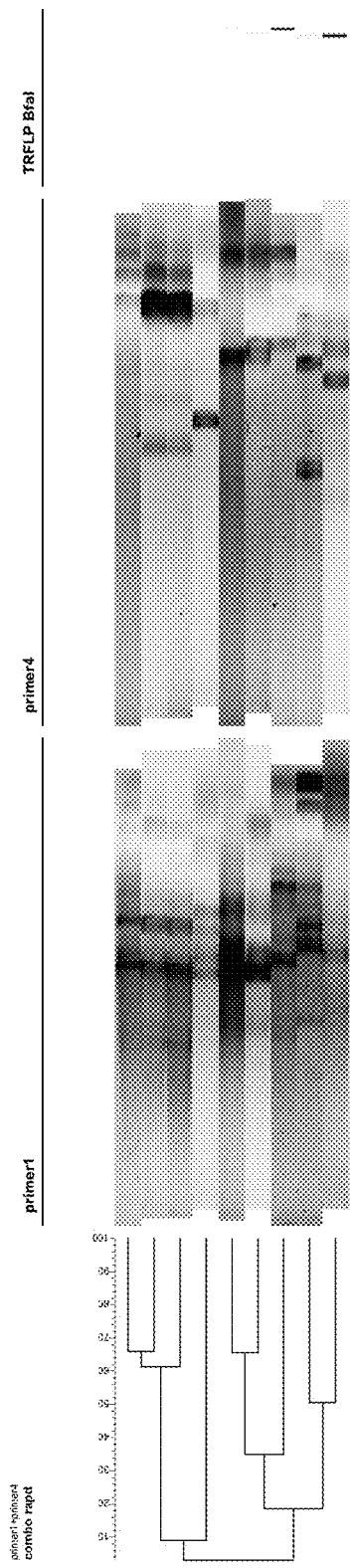
FIG. 2A-2B are two halves of a Dendrogram displaying the similarity between the nine candidate DFM strains as determined by RAPD primer 1 and 4 fingerprints. The TRF banding patterns of the nine strains for the restriction endonucleases Bfa I, Hae III, and Msp I are also shown.
Figure 2B:
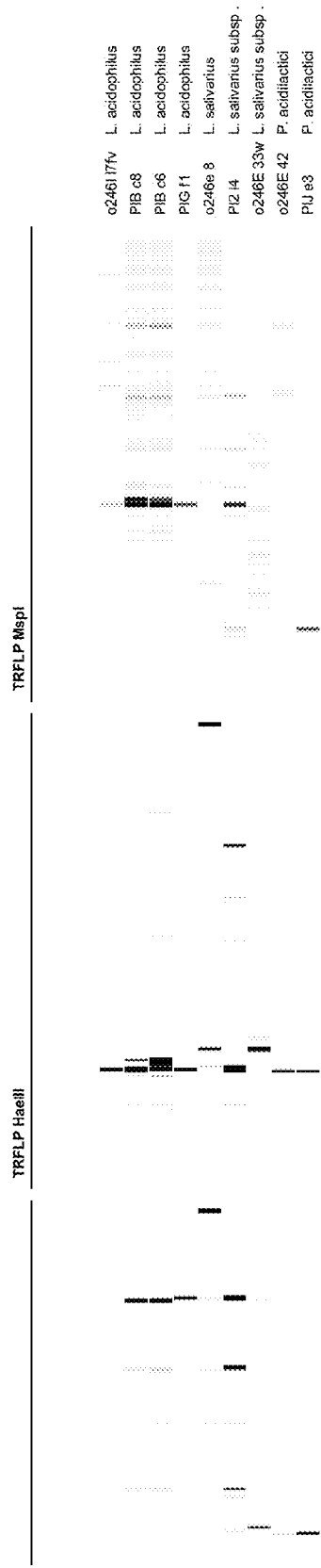

RAPD PCR fingerprints, TRFLP profiles, and the resulting dendrogram associated with nine clusters of RAPDs contained one or more TRF of interest as shown above are displayed in FIG. 2. Four clusters contained TRFs associated with *Lactobacillus acidophilus*, three contained TRFs associated with *Lactobacillus salivarius*, and two contained TRFs associated with *Pediococcus acidilactici*. A representative strain was chosen from each cluster: *L. acidophilus* o246iL7fv, *L. acidophilus* P1Bc8, *L. acidophilus* P1B c6, *L. acidophilus* PLGfl, *L. salivarius* o246e8, *L. salivarius* PL2i4, *L. salivarius* o246e 33w, *P. acidilactici* o246e 42, and *P. acidilactici* P1J e3.

TABLE 12

TRFs of interest determined by correlations associating TRFs to performance and immunology factors.

| Species | On-site/Off-site TRF Length from Example 1 | Indoor/Outdoor TRF Length from Example 2 | TRF Length Rounded Off | TRF Length +/− 2 bps |
|---|---|---|---|---|
| *L. acidophilus* | B100.79 | B100.66 | 101 | 99-103 |
|  | H330.95 | H331.87 | 331-332 | 329-334 |
|  | M189.62 | M189.63 | 190 | 188-192 |
|  | H354.07 | H354.76 | 354-355 | 352-357 |
|  | B269.57 | B270.98 | 270-271 | 268-273 |
| *L. salivarius* | B262.58 | B261.76 | 262-263 | 260-265 |
|  | H279.80 | H278.38 | 279-280 | 277-282 |
| *P. acidilactici* | H337.26 | H336.55 | 337 | 335-339 |
|  | B281.86 | B280.97 | 281-282 | 279-284 |
|  | B279.93 |  | 280 | 278-282 |
|  | B274.93 | B274.94 | 275 | 273-277 |

Identification of these nine candidate strains within a dendrogram encompassing the RAPD profiles from all of the lactic acid bacterial isolates reveals that these nine candidate DFM strains have RAPD profiles that are distinct from each other, even within strains of the same species. For example, *P. acidilactici* strain o246e 42 is only ~10% similar to *P. acidilactici* strain PIJ e3 according to their RAPD profiles, with many bacterial strains of different species having greater similarity to these strains of the same species than they do to each other.

Example 9

Animal Testing of Probiotic Strains to Determine the Benefits of Supplementation During the Pre- and Post-Weaning Periods One strain from each species listed above was selected for initial animal testing to validate the association with the presence of these specific bacteria with improved growth performance in the young pig. Three probiotic strains, including *Lactobacillus acidophilus* P1B c6, *Lactobacillus salivarius* o246e 33w, and *Pediococcus acidilactici* P1J e3, were selected for testing to determine the efficacy of the selected probiotic strains for improving growth performance of young pigs during the pre- and post-weaning production periods.

The three potential probiotic strains, *Lactobacillus acidophilus* P1B c6, *Lactobacillus salivarius* o246e 33w, and *Pediococcus acidilactici* P1J e3, were included in combination in sow diets and individually in nursery pig diets after weaning. Sows were divided into eight treatment groups of four sows per treatment, and litters were randomly assigned to one of eight treatments to determine the effect of administering the probiotic organisms during pre- and post-weaning, and in combination or individually during the nursery period (see Table 13 below). Sows (pre-weaning) were topdressed; for nursery pigs (post-weaning), the DFM was mixed into the diet as part of the complete ration. The eight probiotic treatments were formulated to deliver $1 \times 10^9$ total cfu/pig/day to sows or pigs regardless of whether the total cfu was derived from one organism or a combination of the three selected organisms, with equal amounts (based on CFUs) of each organism included where multiple organisms were used.

TABLE 13

Dietary probiotic treatments administered to sows and their litters during the lactation[1] and nursery[2] phases.

| Treatment | Lactation | Nursery |
|---|---|---|
| 1 | Control | Control |
| 2 | Control | *L. acidophilus* P1B c6 |
| 3 | Control | *L. salivarius* o246e 33w |
| 4 | Control | *P. acidilactici* P1J e3 |
| 5 | *L. acidophilus* P1B c6<br>*L. salivarius* o246e 33w<br>*P. acidilactici* P1J e3 | Control |
| 6 | *L. acidophilus* P1B c6<br>*L. salivarius* o246e 33w<br>*P. acidilactici* P1J e3 | *L. acidophilus* P1B c6<br>*L. salivarius* o246e 33w<br>*P. acidilactici* P1J e3 |
| 7 | Control | *L. acidophilus* P1B c6<br>*L. salivarius* o246e 33w<br>*P. acidilactici* P1J e3 |
| 8[3] | *L. acidophilus* P1B c6<br>*L. salivarius* o246e 33w<br>*P. acidilactici* P1J e3<br>*L. brevis* 1E1 | *L. acidophilus* P1B c6<br>*L. salivarius* o246e 33w<br>*P. acidilactici* P1J e3<br>*L. brevis* 1E1 |

[1]Diets were administered to litters by addition of the probiotic treatment into the sow feed to deliver $1 \times 10^9$ cfu/sow/day.

[2]Probiotic treatments were administered in the nursery pig diet for two weeks following weaning.

[3]*Lactobacillus brevis* was added to the three probiotic combo. *L. brevis* has previously documented benefits to the young pig (Davis et al, 2006).

Contrast statements comparing the three treatments with the three strain combination demonstrate the combination of *L. acidophilus* P1B c6, *L. salivarius* o246e 33w, and *P. acidilactici* P1J e3 when administered to the sow, improves (P=0.03) piglet body weight and average daily gain during the third week of the lactation period (see Table 14 below). Due to the limited replication in the nursery period (4 replications/treatment), any differences in nursery pig performance that may have resulted from the probiotic treatments could not be detected (data not shown).

three direct fed microbial strains at a total count of $1\times10^9$ total cfu/pig/day including $3.34\times10^8$ cfu/pig/day each of *Pediococcus acidilactici* P1J e3, *Lactobacillus salivarius* o246e 33w, and *Lactobacillus acidophilus* P1B c6, (3) A control diet supplemented with two of the direct fed microbial strains at a total count of $1\times10^9$ including $5.0\times10^8$ each of *Pediococcus acidilactici* P1J e3 and *Lactobacillus salivarius* o246e 33w, and (4) A control diet supplemented with $1\times10^9$ of only *Pediococcus acidilactici* P1J e3. All treatments were top dressed to sows.

TABLE 14

Litter performance of pigs nursing sows supplemented with a combination of probiotic strains compared to pigs nursing unsupplemented sows.

| Lactation TRT | Control 1 | Control 2 | Control 3 | Control 4 | L. acidophilus, L. salivarius, P. acidilactici, 5 | L. acidophilus, L. salivarius, P. acidilactici 6 | Control 7 | L. acidophilus, L. salivarius, P. acidilactici L. brevis 8 | SEM | Treatment | P value DFM vs. Control** |
|---|---|---|---|---|---|---|---|---|---|---|---|
| Litter Weight, lbs. | | | | | | | | | | | |
| Initial | 38.50 | 38.53 | 38.73 | 37.35 | 38.95 | 38.78 | 38.75 | 38.65 | 2.00 | 0.70 | 0.35 |
| Period 1 end** | 56.63 | 54.33 | 51.90 | 55.42 | 56.60 | 57.73 | 53.40 | 57.53 | 2.69 | 0.62 | 0.11 |
| Period 2 end** | 98.88 | 98.07 | 93.33 | 97.53 | 100.15 | 106.00 | 94.78 | 101.42 | 6.20 | 0.81 | 0.15 |
| Period 3 end** | 142.85 | 132.25 | 135.00 | 138.75 | 142.38 | 150.95 | 136.25 | 143.50 | 8.55 | 0.77 | 0.15 |
| Litter Size, pigs/sow | | | | | | | | | | | |
| Initial | 11.00 | 11.00 | 11.00 | 11.00 | 11.00 | 11.00 | 11.00 | 11.00 | 0.00 | 1.00 | 1.00 |
| Period 1 end | 11.00 | 10.25 | 10.25 | 11.00 | 10.75 | 10.50 | 10.75 | 11.00 | 0.32 | 0.40 | 0.66 |
| Period 2 end | 10.75 | 10.25 | 10.00 | 10.50 | 10.25 | 10.50 | 10.50 | 10.50 | 0.46 | 0.96 | 0.96 |
| Period 3 end | 10.75 | 9.50 | 9.75 | 10.50 | 10.00 | 10.25 | 10.50 | 10.00 | 0.40 | 0.39 | 0.70 |
| Ave. Pig wt., lbs | | | | | | | | | | | |
| Initial | 3.50 | 3.50 | 3.52 | 3.39 | 3.54 | 3.53 | 3.52 | 3.52 | 0.18 | 0.69 | 0.33 |
| Period 1 end | 5.15 | 5.31 | 5.05 | 5.04 | 5.28 | 5.53 | 4.95 | 5.23 | 0.22 | 0.45 | 0.08 |
| Period 2 end | 9.19 | 9.60 | 9.32 | 9.26 | 9.82 | 10.16 | 9.00 | 9.64 | 0.47 | 0.52 | 0.06 |
| Period 3 end | 13.29 | 13.95 | 13.83 | 13.20 | 14.34 | 14.83 | 12.92 | 14.36 | 0.75 | 0.33 | 0.03 |
| Body wt gain, lbs/d | | | | | | | | | | | |
| Period 1 | 0.38 | 0.40 | 0.34 | 0.36 | 0.39 | 0.45 | 0.32 | 0.39 | 0.04 | 0.37 | 0.09 |
| Period 2 | 0.58 | 0.61 | 0.61 | 0.60 | 0.65 | 0.66 | 0.58 | 0.63 | 0.04 | 0.71 | 0.08 |
| Period 3 | 0.59 | 0.62 | 0.64 | 0.56 | 0.65 | 0.67 | 0.56 | 0.68 | 0.05 | 0.13 | 0.02 |
| Cumulative | 0.53 | 0.57 | 0.56 | 0.53 | 0.59 | 0.61 | 0.51 | 0.59 | 0.04 | 0.34 | 0.03 |

*Values represent the mean of four litters per treatment
**Contrast of Treatments 1, 2, 3, 4, and 7 vs. Treaments 5, 6, and 8

Example 10

Figure 3:
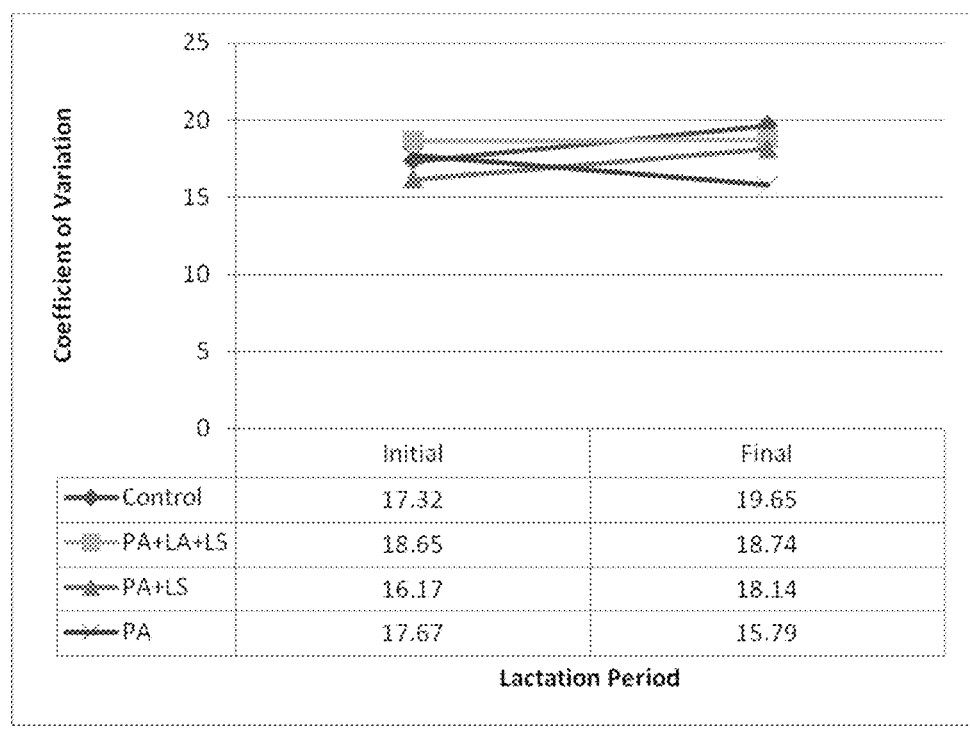
FIG. 3 is a graph displaying initial and final coefficient of variation of body weight within litter resulting from the administration of probiotic combinations to sows during the lactation period (Treatment×time interaction, $P=0.06$; $SE=1.22$). PA=*Pediococcus acidilactici* P1J e3; LA=*Lactobacillus acidophilus* P1B c6; LS=*Lactobacillus salivarius* o246e 33w.

Animal Testing to Confirm and Further Define the Beneficial Response from Supplementation of a Combination of Three Probiotic Strains to Sows During Lactation The beneficial response from feeding the three-strain probiotic combination of *Lactobacillus acidophilus* P1B c6, *Lactobacillus salivarius* o246e 33w, and *Pediococcus acidilactici* P1J e3 to sows during the lactation period was confirmed in a second study that further evaluated these strains by also testing *P. acidilactici* P1J e3 and *L. salivarius* o246e 33w in combination as well as *P. acidilactici* P1J e3 alone in the following treatment arrangement with 20 pens per treatment: (1) A control diet, (2) A control diet supplemented with all Supplementation with the three strain combination again improved (P<0.05) piglet average daily gain during the third week of lactation compared to pigs from unsupplemented sows (see Table 15 below). Although not significantly different from the control, average daily gain of piglets nursing sows supplemented with only *P. acidilactici* P1J e3 was numerically greater, and was similar to piglets nursing sows supplemented with the three strain combination. Supplementation of sows with either the three strain combination or *P. acidilactici* P1J e3 alone prevented an increase in the variation in piglet weight within a litter, and *P. acidilactici* P1J e3 supplementation alone decreased the variation in piglet weight within litter throughout the lactation period (treatment×time interaction, P=0.06; see FIG. 3).

TABLE 15

Pre-weaning litter performance of litters from sows administered probiotic supplements throughout lactation.

| | Treatments[1] | | | | | |
|---|---|---|---|---|---|---|
| | Control | PA + LS + LA | PA + LS | PA | SE | P = |
| Initial Weights at Birth[2] | | | | | | |
| Litter Weight | 36.58 | 37.00 | 37.45 | 37.14 | 0.99 | 0.845 |
| Average Pig Weight | 3.24 | 3.28 | 3.32 | 3.29 | 0.08 | 0.837 |
| Period 1 | | | | | | |
| ADG | 0.37 | 0.39 | 0.36 | 0.39 | 0.02 | 0.562 |
| Litter Weight | 61.17 | 60.18 | 60.04 | 60.44 | 1.97 | 0.964 |
| Average Pig Weight | 5.49 | 5.70 | 5.55 | 5.72 | 0.16 | 0.414 |
| Period 2 | | | | | | |
| ADG | 0.50 | 0.54 | 0.50 | 0.52 | 0.022 | 0.233 |
| Litter Weight | 97.97 | 97.60 | 95.96 | 96.50 | 3.16 | 0.954 |
| Average Pig Weight | 9.26 | 9.69 | 9.20 | 9.75 | 0.276 | 0.143 |
| Period 3 | | | | | | |
| ADG | $0.51^b$ | $0.56^a$ | $0.50^b$ | $0.54^{a,b}$ | 0.019 | 0.027 |
| Litter Wean Weight | 134.39 | 135.94 | 131.22 | 132.26 | 4.47 | 0.807 |
| Average Pig Weight | | | | | | |

[1]PA = *Pediococcus acidilactici* PIJ e3; LS = *Lactobacillus salivarius* o246e 33w; LA = *Lactobacillus acidophilus* PIB c6.
[2]Mean weights after number of pigs per litter were equalized.
[a,b]Means without common superscripts are significantly different at P < 0.05.

Example 11

Animal Testing of Probiotic Strains to Determine the Benefits of Supplementation During the Nursery Phase of Production A total of 480 pigs were weaned, blocked based on initial body weight, and housed four pigs/pen in a total of 120 pens. Six dietary treatments were administered to the nursery pigs during the first two weeks of the nursery period (20 pens/treatment). Dietary treatments were 1) A control diet administered to weanling pigs during the first two weeks of the nursery phase; 2) The control diet supplemented with direct-fed microbial candidate organism *Lactobacillus acidophilus*, P1B c6, at $1 \times 10^9$ cfu/pig/day and administered for two weeks in the nursery diet; 3) The control diet supplemented with direct-fed microbial candidate organism *Lactobacillus salivarius*, o246e 8, at $1 \times 10^9$ cfu/pig/day and administered for two weeks in the nursery diet; 4) The control diet supplemented with direct-fed microbial candidate organism *Lactobacillus salivarius*, P12 i4, at $1 \times 10^9$ cfu/pig/day and administered for two weeks in the nursery diet; 5) The control diet supplemented with direct-fed microbial candidate organism *Lactobacillus salivarius*, o246e 33w, at $1 \times 10^9$ cfu/pig/day and administered for two weeks in the nursery diet; 6) The control diet supplemented with direct-fed microbial candidate organism *Pediococcus acidilactici*, o246e 42, at $1 \times 10^9$ cfu/pig/day and administered for two weeks in the nursery diet.

Common nursery diets were fed to all pigs for the last four weeks of the trial. Pig body weight and feed disappearance was determined weekly, and ADG, ADFI, and feed efficiency were calculated for each pen during the six week trial.

Supplementation with *L. salivarius* o246e 33w improved (p<0.05) feed efficiency during the second week of weaning compared to the unsupplemented pigs and pigs fed *L. salivarius* P12 i4 (Table 15). Although not statistically significant (P>0.05) from the control treatment, pigs fed *P. acidilactici* O246e 42 had the lowest FE during the sixth week of the trial. This same strain and *L. salivarius* O246e 8 resulted in improved (P<0.05) feed efficiency compared to pigs fed *L. acidophilus* P1B c6 and *L. salivarius* P12 i4 (Table 16).

TABLE 16

| | Growth Performance [1] | | | | | | | |
|---|---|---|---|---|---|---|---|---|
| | Dietary Treatments[2] | | | | | | | |
| | 1 Control | 2 PIB c6 | 3 o246e 8 | 4 PI2 i4 | 5 o246i 33w | 6 o246e 42 | SEM[3] | P-value |
| Start weight | $14.21^b$ | $14.28^{ab}$ | $14.25^{ab}$ | $14.19^b$ | $14.20^b$ | $14.35^a$ | 0.35 | 0.036 |
| Week 1 weight | 16.86 | 16.74 | 16.59 | 16.85 | 16.73 | 16.90 | 0.38 | 0.866 |
| ADG | 0.33 | 0.31 | 0.29 | 0.33 | 0.32 | 0.32 | 0.02 | 0.808 |
| ADFI | 0.38 | 0.36 | 0.36 | 0.38 | 0.37 | 0.37 | 0.02 | 0.937 |
| FE[4] | 1.27 | 1.28 | 1.30 | 1.22 | 1.22 | 1.23 | 0.08 | 0.928 |
| Week 2 weight | 21.34 | 21.14 | 20.92 | 20.94 | 21.25 | 21.55 | 0.51 | 0.660 |
| ADG | 0.73 | 0.73 | 0.72 | 0.68 | 0.74 | 0.78 | 0.04 | 0.223 |
| ADFI | 0.76 | 0.74 | 0.73 | 0.74 | 0.73 | 0.79 | 0.03 | 0.580 |
| FE | $1.07^{ab}$ | $1.02^{bc}$ | $1.02^{bc}$ | $1.10^a$ | $1.00^c$ | $1.02^{bc}$ | 0.03 | 0.004 |

TABLE 16-continued

Growth Performance [1]

| | Dietary Treatments[2] | | | | | | | |
|---|---|---|---|---|---|---|---|---|
| | 1 Control | 2 PlB c6 | 3 o246e 8 | 4 Pl2 i4 | 5 o246i 33w | 6 o246e 42 | SEM[3] | P-value |
| Week 3 weight | 27.33 | 27.29 | 27.06 | 26.99 | 27.17 | 27.75 | 0.63 | 0.880 |
| ADG | 0.74 | 0.77 | 0.76 | 0.76 | 0.74 | 0.77 | 0.03 | 0.937 |
| ADFI | 1.05 | 1.05 | 1.05 | 1.02 | 1.04 | 1.09 | 0.04 | 0.768 |
| FE | 1.44 | 1.39 | 1.41 | 1.36 | 1.41 | 1.43 | 0.04 | 0.582 |
| Week 4 weight | 34.48 | 34.81 | 34.06 | 34.71 | 34.67 | 34.99 | 0.89 | 0.880 |
| ADG | 1.02 | 1.08 | 1.00 | 1.10 | 1.05 | 1.04 | 0.07 | 0.414 |
| ADFI | 1.47 | 1.49 | 1.45 | 1.52 | 1.49 | 1.48 | 0.07 | 0.854 |
| FE | 1.53 | 1.40 | 1.58 | 1.44 | 1.48 | 1.61 | 0.09 | 0.207 |
| Week 5 weight | 44.01 | 44.55 | 43.46 | 44.41 | 43.74 | 44.76 | 1.11 | 0.783 |
| ADG | 1.36 | 1.39 | 1.32 | 1.37 | 1.30 | 1.39 | 0.05 | 0.562 |
| ADFI | 1.91 | 1.97 | 1.82 | 1.93 | 1.85 | 1.95 | 0.08 | 0.296 |
| FE | 1.41 | 1.42 | 1.37 | 1.42 | 1.43 | 1.40 | 0.03 | 0.465 |
| Week 6 weight | 53.56 | 54.08 | 53.10 | 53.93 | 53.39 | 54.79 | 1.27 | 0.804 |
| ADG | 1.37 | 1.36 | 1.38 | 1.36 | 1.38 | 1.43 | 0.06 | 0.888 |
| ADFI | 2.15 | 2.21 | 2.11 | 2.20 | 2.12 | 2.18 | 0.08 | 0.916 |
| FE | $1.59^{ab}$ | $1.63^{a}$ | $1.54^{b}$ | $1.65^{a}$ | $1.56^{ab}$ | $1.53^{b}$ | 0.04 | 0.049 |
| Cumulative | | | | | | | | |
| ADG | 0.90 | 0.93 | 0.89 | 0.92 | 0.90 | 0.94 | 0.03 | 0.591 |
| ADFI | 1.26 | 1.29 | 1.23 | 1.28 | 1.25 | 1.30 | 0.04 | 0.562 |
| FE | 1.40 | 1.39 | 1.38 | 1.39 | 1.38 | 1.38 | 0.01 | 0.551 |

[1] Data are means of 20 replicates of six treatments.
[2] Dietary treatments were treatment 1 = Control, treatment 2 = control diet supplemented with direct-fed microbial candidate organism Lactobacillus acidophilus, PlB c6, at $1 \times 10^9$ cfu/pig/day, treatment 3 = control diet supplemented with direct-fed microbial candidate organism Lactobacillus salivarius, o246e 8, at $1 \times 10^9$ cfu/pig/day, treatment 4 = control diet supplemented with direct-fed microbial candidate organism Lactobacillus salivarius, Pl2 i4, at $1 \times 10^9$ cfu/pig/day, treatment 5 = control diet supplemented with direct fed
microbial candidate organism Lactobacillus salivarius, o246i 33w, at $1 \times 10^9$ cfu/pig/day, treatment 6 = control diet supplemented with direct-fed microbial candidate organism Pediococcus acidilactici, o246e 42, at $1 \times 10^9$ cfu/pig/day
[3] standard error of the mean (SEM)
[4] feed efficiency (FE)
[abc] Means within a row with different superscripts are significantly different (P < 0.05)

Example 12

Identification of Probiotic Bacteria Based on Negative Correlations to Potentially Pathogenic Bacteria Correlations can be made associating presence of specific TRFs in the gastrointestinal tract representing selected probiotic strains with the presence of pathogen defined TRFs, allowing the prediction of how administration of the probiotic bacteria impact the presence of pathogenic organisms in these tissues in the young pig. The presence of TRFs defined as *L. acidophilus* (Table 17) and *L. salivarius* (Table 18) correlated negatively (P<0.05) to the presence of several pathogen-defined TRFs defined as *Clostridium, Mycobacterium*, and *Pasteurella* spp indicating that when these probiotic bacteria were present in the gastrointestinal tract, these pathogens were less likely to be present.

TABLE 17

Terminal restriction fragments (TRFs) that were negatively correlated to the presence of *L. acidophilus*-defined TRFs (B100.79, H330.95, M189.62) in the gastrointestinal tracts of pigs.

| | | *L. acidophilus* | |
|---|---|---|---|
| | TRF | Correlation P value | Putative Identification |
| B100.79 | | | |
| | H231.09 | 0.034 | *Clostridium* spp., *Mycobacterium* spp. |
| | H180.00 | 0.012 | *Mycobacterium* spp. |
| H330.95 | | | |
| | H231.09 | 0.001 | *Clostridium* spp., *Mycobacterium* spp. |
| | M281.97 | 0.003 | *Mycobacterium* spp. |
| | M474.33 | 0.011 | *Clostridium* spp. |
| | H256.70 | 0.021 | *Pasteurella* spp. |
| | H258.50 | 0.047 | *Clostridium* spp. |
| M189.62 | | | |
| | B279.93 | 0.027 | *Pasteurella* spp. |

TABLE 18

Terminal restriction fragments (TRFs) that were negatively correlated to the presence of *L. salivarius*-defined TRFs in the gastrointestinal tracts of pigs.

| TRF | Correlation P value | Putative Identification |
|---|---|---|
| B262.58 | | |
| H231.09 | 0.016 | *Clostridium* spp., *Mycobacterium* spp. |
| M281.97 | 0.016 | *Mycobacterium* spp. |
| H180.00 | 0.018 | *Mycobacterium* spp. |
| B336.73 | 0.034 | *Clostridium* spp. |
| M474.33 | 0.037 | *Clostridium* spp. |
| M71.77 | 0.048 | *Mycobacterium* spp. |
| B55.08 | 0.008 | *Clostridium* spp. |
| H301.08 | 0.004 | *Clostridium* spp. |
| H279.80 | | |
| M474.33 | 0.050 | *Clostridium* spp. |

It is understood that the various embodiments are shown and described above to illustrate different possible features of the invention and the varying ways in which these features may be combined. Apart from combining the different features of the above embodiments in varying ways, other modifications are also considered to be within the scope of the invention. The invention is not intended to be limited to the embodiments described above, but rather is intended to be limited only by the claims set out below. Thus, the invention encompasses all alternate embodiments that fall literally or equivalently within the scope of these claims.

BIBLIOGRAPHY

Adami, A., A. Sandrucci and V. Cavazzoni. 1997. Piglets fed from birth with the probiotic *Bacillus coagulans* as additive: zootechnical and microbiological aspects. Ann Microbiol. Enzimol. 47: 139-149.

Baker, G. C., J. J. Smith, and D. A. Cowan. 2003. Review and re-analysis of domain-specific 16S primers. Journal of Microbiological Methods. 55:541-555.

Bikker, P., A. J. van Dijk, A. Dirkzwager, J. Fledderus, M. Ubbink-Blanksma, and A. C. Beynen. 2004. The influence of diet composition and an anti-microbial growth promoter on the growth response of weaned piglets to spray dried animal plasma. Livestock Prod. Sci. 86:201-208.

Bosi, P. I. Han, H. Jung, K. Heo, S. Perini, A. Castellazzi, L. Casini, D. Creston and C. Gremokolini. 2001. Effect of different spray dried plasmas on growth, ileal digestibility, nutrient deposition, immunity and health of early-weaned pigs challenged with *E. coli* K88. Asian-Aust. J. Anim. Sci. 14:1138-1143.

Bosi, P., L. Casini, A. Finamore, C. Cremokolini, G. Merialdi, P. Trevisi, F. Nobili, and E. Mengheri. 2004. Spray-dried plasma improves growth performance and reduces inflammatory status of weaned pigs challenged with enterotoxigenic *Escherichia coli* K88. J. Anim. Sci. 82:1764-1772.

Brown, D. C., C. V. Maxwell, G. F. Erf, M. E. Davis, S. Singh, and Z. B. Johnson. 2006a. The influence of different management systems and age on intestinal morphology, immune cell numbers and mucin production from goblet cells in post-weaning pigs. Vet. Immunol Immunopath. 111:187-198.

Brown, D. C., C. V. Maxwell, G. F. Erf, M. E. Davis, S. Singh, and Z. B. Johnson. 2006b. Ontogeny of T lymphocytes and intestinal morphological characteristics in neonatal pigs at different ages in the postnatal period. J. Anim. Sci. 84:567-578.

Cera, K. R., D. C. Mahan, R. F. Cross, G. A. Reinhart, and R. E. Whitmoyer. 1988. Effect of age, weaning and post-weaning diet on small intestinal growth and small intestinal morphology in young swine. J. Anim. Sci. 66:574.

Casey, P. G., G. E. Gardiner, G. Casey, B. Bradshaw, P. G. Lawlor, P. B. Lynch, F. C. Leonard, C. Stanton, R. P. Ross, G. F. Fitzgerald, and C. Hill. 2007. A five-strain probiotic combination reduces pathogen shedding and alleviates disease signs in pigs challenged with *Salmonella enterica* serovar Typhimurium. Appl. Environ. Microbiol. 73:1858-1863.

Coffey, R., G. Cromwell. 1995. The impact of environment and antimicrobial agents on the growth response of early weaned pigs to spray-dried porcine plasma. J. Anim. Sci. 73: 2532-2539.

Cromwell, G. L. 2001. Antimicrobial and promicrobial agents. In: A. J. Lewis and L. L. Southern (eds.) Swine Nutrition. P. 611. CRC Press, Boca Raton, Fla.

Davis, M. E., D. C. Brown, M. S. Dirain, H. D. Dawson, C. Maxwell, and T. Rehberger. 2006. Comparison of direct-fed microbial and antibiotic supplementation on innate and adaptive immune characteristics of weaning pigs. Reprod. Nutr. Dev. 46(Suppl. 1):S63.

Davis. M. E., D. C. Brown, A. Baker, K. Bos, M. S. Dirain, E. Halbrook, Z. B. Johnson, C. Maxwell, and T. Rehberger. 2007. Effect of direct-fed microbial and antibiotic supplementation on gastrointestinal microflora, mucin histochemical characterization, and immune populations of weanling pigs. Livestock. Sci. 108:249-253.

Davis, M. E., C. V. Maxwell, G. F. Erf, D. C. Brown, and T. J. Wistuba. 2004. Dietary supplementation with phosphorylated mannans improves growth response and modulates immune function in weanling pigs. J. Anim. Sci. 82:1882-1891.

Dritz, S., M. Chengappa, J. Nelssen, M. Tokach, R. Goodband, J. Nietfeld, and J. Staats. 1996. Growth and microbial flora of nonmedicated, segregated, early weaned pigs from a commercial swine operation. JAVMA 208:711.

Fangman, T., M. Roderick and C. Tubbs. 1997. Segregated early weaning. Swine Health Prod. 5:195.

Fuller, R. 1997. Introduction. In: R. Fuller (Ed.). Probiotics 2: applications and practical aspects. Chapman and Hall, New York. P. 1.

Gaskins, H. R. 2001. Intestinal bacteria and their influence on swine growth In: Austin J. Lewis and Lee L. Southern (Ed.). Swine Nutrition $2^{nd}$ Edition. P 585-608.

Hammer, C., J. Quigley, L. Riberio, and H. Tyler. 2004. Characterization of a colostrum replacer and a colostrum supplement containing IgG concentrate and growth factors. J. Dairy. Sci. 87:106-111.

Kyriakis, S. C., V. K. Tsiloyiannis, J. Vlemmas, K. Sarris, A. C. Tsinas, C. Alexopoulos, and I. Jansegers. 1999. The effect of probiotic LSP 122 on the control of post-weaning diarrhea syndrome of piglets. Res. Vet. Sci. 67:223-228.

Marsh, T., P. Saxman, J. Cole, and J. Tiedje. 2000. Terminal restriction fragment length polymorphism analysis web-based research tool for microbial community analysis. Appl Environ Microbiol 66:3616-3620.

Maxwell, Jr., C. V. and S. D. Carter. 2001. Feeding Weanling Pigs. In: Austin J. Lewis and Lee L. Southern (Ed.). Swine Nutrition $2^{nd}$ Edition. P 691-717.

McCracken, B. A., Gaskins, H. R., Ruwe-Kaiser, P. J., Klasing, K. C., Jewell, D. E. 1995. Diet-dependent and diet-independent metabolic responses underlie growth stasis of pigs at weaning. J. Nutr. 125, 2838-2845.

Mouricout, M. A., and R. A. Julien. 1986 Inhibition of mannose-resistant Hae magglutination of sheep erythrocytes by enterotoxigenic *Escherichia coli* in the presence of plasma glycoprotein glycans. FEMS Microbiol. Lett. 37:145-149.

Nollet, H., P. Deprez, E. van Driessche, E. Muylle. 1999. Protection of just weaned pigs against infection with F18+ *Escherichia coli* by non-immune plasma powder. Vet. Microbiol. 65:37-45.

Perez-Bosque, A., C. Pelegri, M. Vicario, M. Castell, L. Russell, J. Campbell, J. Quigley, J. Polo, C. Amat, and M. Morteo. 2004. Dietary plasma protein affects the immune response of weaned rats challenged with *S. aureus* Superantigen B. J. Nutr. 134:2667-2672.

Roche, K. C. Martins, R. Cosme, R. Fayer, R. Guerrant. 2000. Transforming growth factor beta-1 ameliorates intestinal epithelial barrier disruption by *Cryptosporidium parvum* in the absence of mucosal T lymphocytes. Infect. Immun 68:5635-5644.

Tang, M., B. Laarveld, A. G. Van Kessel, D. L. Hamilton, A. Estrada, and J. F. Patience. 1999. Effect of segregated early weaning on postweaning small intestinal development in pigs. J. Anim. Sci. 77:3191.

Tannock, G. W. 2004. A special fondness for lactobacilli. Appl. Environ, Microbiol. 70:3189-3194.

Torrallardona, D., M. Conde, I. Badiola, J. Polo, and J. Brufau. 2003. Effect of fishmeal replacement with spray-dried plasma and colistin on intestinal structure, intestinal microbiology, and performance of weanling pigs challenged with *Escherichia coli* K99. J. Anim. Sci. 81:1220-1226.

van Dijk, A., H. Everts, M. Nabuurs, R. Margry, and A. Beynen. 2001a. Growth performance of weanling pigs fed spray-dried animal plasma: a review. Livestock Production Science. 68:263-274.

van Dijk, A., R. Margry, A. Van Der Lee, G. Hemke, and A. Beynen. 2002b. Growth performance and health status in weanling piglets fed spray-dried porcine plasmas under typical Northern European conditions. J. Anim. Physiol. Anim. Nutr. (Berl). 86:17-25.

Wilson, M, 1995. Segregated early weaning. Pig Lett. 15:17-20.

Yang, H., J. Lopez, C. Risley, T. Radice and D. Holzgraefe. 2003. Effect of adding a *bacillus* based direct fed microbial on performance of nursery pigs fed diets with or without antibiotics. J. Anim. Sci.

What is claimed is:

1. A method comprising administering to an animal an effective amount of *Lactobacillus acidophilus* strain P1B c6 (NRRL B-50103) to improve growth performance of said animal.

2. The method of claim 1, wherein the animal is a pig.

3. The method of claim 2, wherein about $1\times10^8$ total cfu/pig/day to about $5\times10^{10}$ total cfu/pig/day of the strain or strains is administered to the pig.

4. The method of claim 1, wherein the animal is a sow.

5. The method of claim 4, wherein the sow is a lactating sow.

6. The method of claim 4, wherein administering said strain to said animal improves body weight and average daily gain in piglets borne to the sow relative to that in piglets borne to sows that have not been administered the strain.

7. The method of claim 4, wherein administering said strain to said animal prevents an increase in variation in piglet weight within a litter borne to the sow relative to that in piglets borne to sows that have not been administered the strain.

8. The method of claim 4, wherein administering said strain to said animal prevents an increase in variation in piglet weight within a litter borne to the sow relative to that in piglets borne to sows that have not been administered the strain.

9. The method of claim 4, wherein administering said strain to said animal decreases variation in piglet weight within a litter borne to the sow relative to that in piglets borne to sows that have not been administered the strain.

10. The method of claim 1, wherein the animal is a pig in the nursery phase of production.

11. The method of claim 1, wherein administering said strain to the animal modulates the immune system of the animal.

* * * * *